United States Patent
Kim

(10) Patent No.: US 12,046,377 B2
(45) Date of Patent: Jul. 23, 2024

(54) HEALTH CARE SYSTEM, HEALTH CARE SERVER, AND HEALTH CARE METHOD FOR PROVIDING RESPIRATORY TREATMENT INFORMATION USING AIR QUALITY INFORMATION

(71) Applicant: INTIN CO., LTD., Daegu-si (KR)

(72) Inventor: Ji Hoon Kim, Seoul (KR)

(*) Notice: Subject to any disclaimer, the term of this patent is extended or adjusted under 35 U.S.C. 154(b) by 0 days.

(21) Appl. No.: 17/262,444

(22) PCT Filed: Aug. 10, 2020

(86) PCT No.: PCT/KR2020/010617
§ 371 (c)(1),
(2) Date: Jan. 22, 2021

(87) PCT Pub. No.: WO2021/045401
PCT Pub. Date: Mar. 11, 2021

(65) Prior Publication Data
US 2022/0301725 A1    Sep. 22, 2022

(30) Foreign Application Priority Data
Sep. 2, 2019 (KR) .................. 10-2019-0108055

(51) Int. Cl.
*G16H 70/20* (2018.01)
*G01N 33/00* (2006.01)
*G16H 10/20* (2018.01)

(52) U.S. Cl.
CPC ......... *G16H 70/20* (2018.01); *G01N 33/0062* (2013.01); *G16H 10/20* (2018.01)

(58) Field of Classification Search
CPC ........ G16H 70/20; G16H 10/20; G16H 10/60; G16H 20/40; G16H 20/00; G16H 30/20;
(Continued)

(56) References Cited

U.S. PATENT DOCUMENTS

2009/0265186 A1   10/2009   Tarassenko et al.
2012/0103330 A1*  5/2012    David ............... C23C 16/325
                                              128/203.12
(Continued)

FOREIGN PATENT DOCUMENTS

AU   2016343818 A1 *  6/2018  ........... A61B 5/0022
JP   2019-520091 A     7/2019
(Continued)

OTHER PUBLICATIONS

Singla et al., Towards an integrated framework for air quality monitoring and exposure estimation—a review, Aug. 31, 2018, Springer Nature Switzerland, pp. 1-21. (Year: 2018).*

(Continued)

*Primary Examiner* — Christopher L Gilligan
(74) *Attorney, Agent, or Firm* — ANTONIO HA & U.S. PATENT, LLC

(57) ABSTRACT

Disclosed are a health care system, a health care server, and a health care method for providing respiratory treatment information using air quality information. The health care system includes an air quality measurement unit located in at least one of the inside or outside of a building and configured to transmit air quality information on a specific location, which is an area or space in which a user is located, a user terminal configured to transmit user identification information for identifying the user and user location information on a specific location where the user is located, and a health care server configured to receive the air quality information, the user identification information, and the user location information and to provide treatment information on the user's respiratory system using analysis information analyzed from the air quality information of the area where the user is located.

37 Claims, 18 Drawing Sheets

(58) Field of Classification Search
CPC . G01N 33/0062; G01N 33/00; G01N 33/0004
See application file for complete search history.

(56) References Cited

U.S. PATENT DOCUMENTS

| | | | | |
|---|---|---|---|---|
| 2016/0361452 | A1* | 12/2016 | Blackley | A61L 9/14 |
| 2018/0325422 | A1* | 11/2018 | Sokol | A62B 7/10 |
| 2019/0004023 | A1* | 1/2019 | Kelly | G01D 3/08 |
| 2020/0253547 | A1* | 8/2020 | Harris | A61B 5/0022 |
| 2020/0281518 | A1* | 9/2020 | Salorinne | G16H 10/65 |
| 2020/0390400 | A1* | 12/2020 | Ssenyange | G16H 20/10 |
| 2022/0230723 | A1* | 7/2022 | Wieczorek | G16H 20/17 |

FOREIGN PATENT DOCUMENTS

| | | |
|---|---|---|
| JP | 2018-531055 A | 9/2019 |
| KR | 10-2018-0105798 | 10/2018 |
| KR | 10-1940452 | 1/2019 |
| KR | 10-2019-0024500 | 3/2019 |
| KR | 10-2013831 | 8/2019 |

OTHER PUBLICATIONS

English Specification of JP2018-531055A.
English Specification of JP2019-520091A.
English Specification of 10-1940452.
English Specification of 10-2018-0105798.
English Specification of 10-2019-0024500.
English Specification of 10-2013831.

* cited by examiner

FIG. 12

| Air quality information | Treatment program 1 | | | | Treatment program 2 | | | | Treatment program 3 | | | | Treatment program 4 | | | |
|---|---|---|---|---|---|---|---|---|---|---|---|---|---|---|---|---|
| | E1 | E2 | E3 | E4 | E1 | E2 | E3 | E4 | E1 | E2 | E3 | E4 | E1 | E2 | E3 | E4 |
| Good (◎) | – | – | – | – | – | – | – | – | 1 min. /once | – | – | – | 2 min. /once | – | – | – |
| Normal (○) | 1 min. /once | – | – | – | 2 min. /once | – | – | – | 2 min. /twice | 1 min. /once | – | – | 2 min. /twice | 1 min. /twice | – | 1 min. /once |
| Slightly poor (△) | 2 min. /twice | 1 min. /once | – | – | 2 min. /twice | 2 min. /once | 1 min. /once | 1 min. /once | 2 min. /twice | 2 min. /twice | 1 min. /once | 1 min. /once | 2 min. /twice | 2 min. /twice | 2 min. /once | 2 min. /once |
| Very poor (✕) | 2 min. /twice | 2 min. /once | 1 min. /once | 1 min. /once | 2 min. /twice | 3 min. /twice | 2 min. /once | 2 min. /once | 3 min. /twice | 3 min. /twice | 2 min. /once | 2 min. /once | 3 min. /twice | 3 min. /twice | 3 min. /once | 3 min. /once |
| Exposure time information | Short (◎) | | | | Normal (○) | | | | Slightly long (△) | | | | very long (✕) | | | | light ←→ heavy

E1 – nebulizer, E2 – injector, E3 – inhaler, E4 – rhinitis treatment instrument
Air quality information: good (◎), normal (○), slightly poor (△), very poor (✕)
Exposure time information: short (◎), normal (○), slightly poor (△), very poor (✕)

FIG. 13

| Air quality information | Treatment program 1 ||||| Treatment program 2 ||||| Treatment program 3 ||||| Treatment program 4 ||||| User treatment history information |
|---|---|---|---|---|---|---|---|---|---|---|---|---|---|---|---|---|---|---|
| | E1 | E2 | E3 | E4 | E1 | E2 | E3 | E4 | E1 | E2 | E3 | E4 | E1 | E2 | E3 | E4 | |
| Good (◎) | – | – | – | – | – | – | – | – | 1 min. /once | – | – | – | 2 min. /once | – | – | – | Better (◎), maintained (○), worse (△), deteriorated (✕) Maintained (○), case before three days |
| Normal (○) | 1 min. /once | – | – | – | 2 min. /once | 1 min. /once | – | – | 2 min. /twice | 1 min. /once | – | – | 2 min. /twice | 1 min. /twice | – | 1 min. /once | Maintained (○), case three days ago |
| Slightly poor (△) | 2 min. /twice | 1 min. /once | – | – | 2 min. /twice | 2 min. /twice | 1 min. /once | 1 min. /once | 2 min. /twice | 2 min. /twice | 1 min. /once | 1 min. /once | 2 min. /twice | 2 min. /twice | 2 min. /once | 2 min. /once | Maintained (○), case three days ago |
| Very poor (✕) | 2 min. /twice | 2 min. /twice | 1 min. /once | 1 min. /once | 2 min. /twice | 2 min. /twice | 2 min. /once | 2 min. /once | 3 min. /twice | 3 min. /twice | 2 min. /once | 2 min. /once | 3 min. /twice | 3 min. /twice | 3 min. /once | 3 min. /once | Maintained (○), case three days ago |
| Exposure time information | Short (◎) |||| Normal (○) |||| Slightly long (△) |||| very long (✕) |||| | light ⟷ heavy

E1 – nebulizer, E2 – injector, E3 – inhaler, E4 – rhinitis treatment instrument
Air quality information: good (◎), normal (○), slightly poor (△), very poor (✕)
Exposure time information: short (◎), normal (○), slightly poor (△), very poor (✕)
User treatment history information – diagnosis history – better (◎), maintained (○), worse (△), deteriorated (✕)
– treatment history – one day ago, two days ago, three days ago, four days ago

FIG. 14

| Air quality information | Treatment program 1 | | | | Treatment program 2 | | | | Treatment program 3 | | | | Treatment program 4 | | | | User treatment history information | Current status information |
|---|---|---|---|---|---|---|---|---|---|---|---|---|---|---|---|---|---|---|
| | E1 | E2 | E3 | E4 | E1 | E2 | E3 | E4 | E1 | E2 | E3 | E4 | E1 | E2 | E3 | E4 | | |
| Good (◎) | 2 min. /twice | 1 min. /once | — | 1 min. /once | 2 min. /twice | 2 min. /twice | 1 min. /once | 1 min. /once | 2 min. /twice | 2 min. /twice | 1 min. /once | 1 min. /once | 2 min. /twice | 2 min. /twice | 2 min. /once | 2 min. /once | Maintained (○), case three days ago | Case of slightly serious (△) |
| Normal (○) | 2 min. /twice | 2 min. /twice | 1 min. /once | 1 min. /once | 3 min. /twice | 3 min. /twice | 2 min. /twice | 2 min. /twice | 3 min. /twice | 3 min. /twice | 2 min. /twice | 2 min. /once | 3 min. /twice | 3 min. /twice | 3 min. /once | 3 min. /once | Maintained (○), case three days ago | Case of slightly serious (△) |
| Slightly poor (△) | 3 min. /twice | 3 min. /twice | 1 min. /once | 1 min. /once | 3 min. /twice | 3 min. /twice | 2 min. /twice | 2 min. /twice | 3 min. /thrice | 3 min. /thrice | 3 min. /twice | 3 min. /twice | 3 min. /thrice | 3 min. /thrice | 2 min. /twice | 2 min. /twice | Maintained (○), case three days ago | Case of slightly serious (△) |
| Very poor (X) | 3 min. /twice | 3 min. /twice | 1 min. /once | 1 min. /once | 3 min. /thrice | 3 min. /thrice | 2 min. /twice | 2 min. /twice | 3 min. /thrice | 3 min. /thrice | 3 min. /twice | 3 min. /twice | 3 min. /thrice | 3 min. /thrice | 3 min. /thrice | 3 min. /thrice | Maintained (○), case three days ago | Case of slightly serious (△) |
| Exposure time information | Short (◎) | | | | Normal (○) | | | | Slightly long (△) | | | | very long (X) | | | | | | light ←→ heavy

E1 – nebulizer, E2 – injector, E3 – inhaler, E4 – rhinitis treatment instrument
Air quality information: good(◎), normal(○), slightly poor(△), very poor(X)
Exposure time information: short (◎), normal(○), slightly poor(△), very poor(X)
User treatment history information – diagnosis history
└ better (◎), maintained (○), worse (△), deteriorated (x)
  treatment history – one day ago, two days ago, three days ago, four days ago
Current status information: good (◎), normal (○), slightly poor (△), very poor (x)

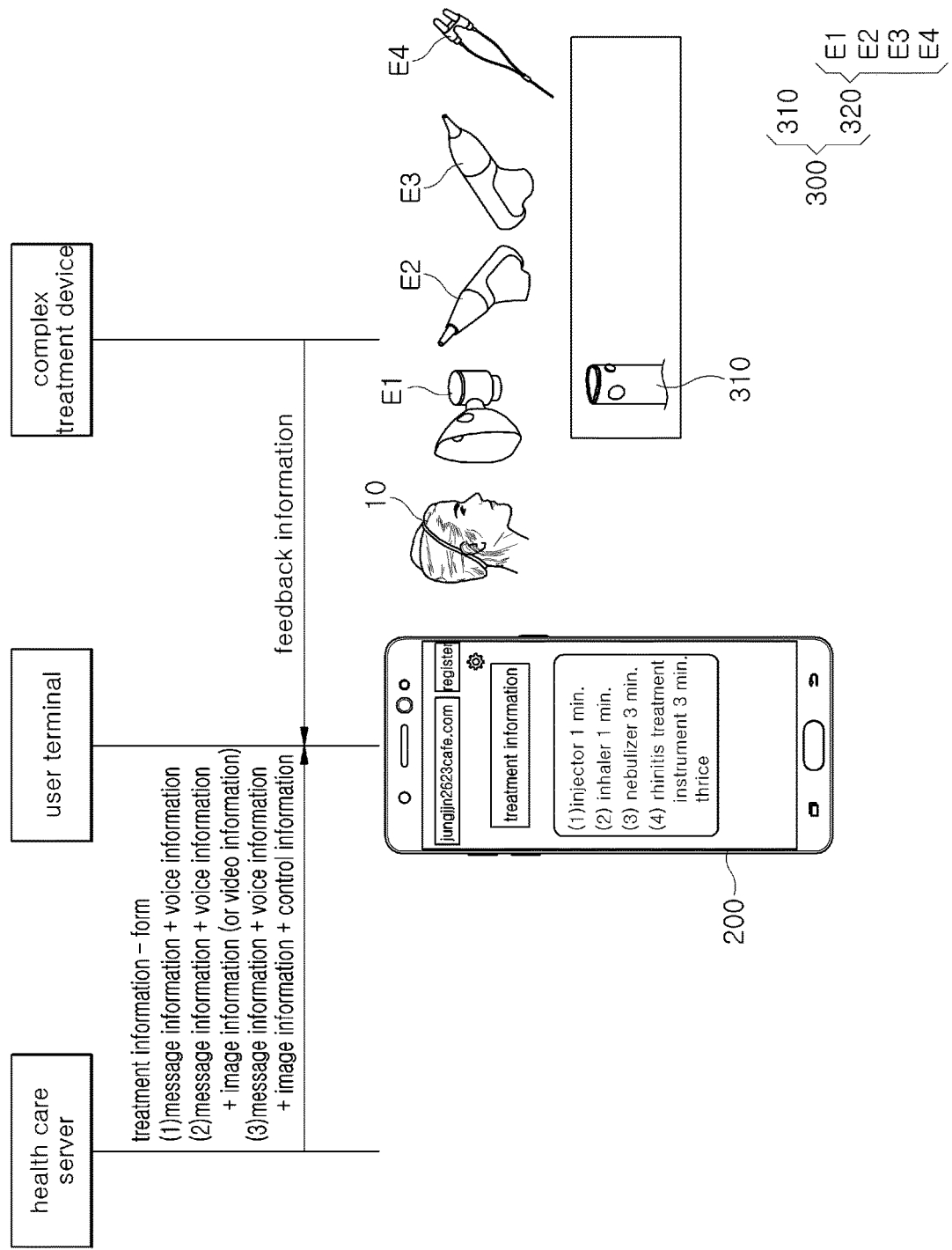

HEALTH CARE SYSTEM, HEALTH CARE SERVER, AND HEALTH CARE METHOD FOR PROVIDING RESPIRATORY TREATMENT INFORMATION USING AIR QUALITY INFORMATION

TECHNICAL FIELD

The present disclosure relates to a health care system, a health care server, and a health care method for providing respiratory treatment information using air quality information, and more particularly, to a health care system, a health care server, and a health care method for providing respiratory treatment information using air quality information on a user's respiratory system.

BACKGROUND ART

As the industry has developed, the degree of pollution of a natural environment has gradually increased, and due to this, the frequency of occurrence of diseases due to air pollution has increased to shorten a lifespan.

Therefore, the degree of outdoor air pollution is measured and notified every day at a national level and recommendations such as refraining from going out are provided according to levels of air pollution.

Accordingly, a ultraviolet (UV) index, a lung health index, a current weather condition, temperature and humidity, and the like are notified to the outside using the degree of outdoor air quality, environmental information, and the like.

In addition, as the degree of pollution of outdoor air increases day by day, an indoor air condition is also unsafe and health of modern people who spend a lot of time living indoors is also unsafe.

In particular, in recent years, air quality due to fine dust has become a major issue as a social problem and resultant respiratory-related diseases tend to increase significantly.

Nevertheless, most people live with quite a bit of discomfort and use specialized medical institutions only when pain or discomfort that is hard to bear occurs.

In order to alleviate such inconvenience, technologies that frequently check physical conditions using various high-tech equipment and transmit checked physical conditions to specialized medical institutions through a network to check the physical conditions have been developed but rarely commercialized and used.

DISCLOSURE

Technical Problem

An aspect of the present disclosure provides a health care system, a health care server, and a health care method for providing respiratory treatment information using air quality information that may be conveniently used by users, and more particularly, a health care system, a health care server, and a health care method for providing respiratory treatment information using air quality information that is more conveniently available to users regarding a condition of a user's respiratory system and a treatment related thereto.

Technical Solution

In an aspect, a health care system for providing respiratory treatment information using air quality information, includes: an air quality measurement unit located in at least one of the inside or outside of a building and configured to transmit air quality information on a specific location, which is an area or space in which a user is located; a user terminal configured to transmit user identification information for identifying the user and user location information on a specific location where the user is located; and a health care server configured to receive the air quality information, the user identification information, and the user location information and to provide treatment information on the user's respiratory system using analysis information analyzed from the air quality information of the area where the user is located.

The air quality information may be transmitted from the air quality measurement unit to the health care server through a communication network linked with the air quality measurement unit or may be transmitted from the air quality measurement unit to the health care server through the user terminal.

The air quality measurement unit may include an indoor air quality measurer provided inside the building and an outdoor air quality measurer provided outside the building, and the air quality information may include indoor air quality information on at least one of fine dust concentration, ultrafine dust concentration, temperature, humidity, oxygen concentration, carbon dioxide, nitrogen oxide concentration, formaldehyde concentration, benzene concentration, toluene concentration, alcohol concentration, methane gas concentration, cigarette smoke concentration, and radon provided from the indoor air quality measurer; and outdoor air quality information on at least one of an outdoor temperature, a fine dust concentration, an ultrafine dust concentration, the degree of ultraviolet (UV) light, an outdoor air quality index, and a concentration of a criteria air pollutant.

The outdoor air quality index may be an integrated atmospheric environment index, and the criteria air pollutant may include at least one of $SO_2$, $CO$, $O_3$, and $NO_2$.

The user location information transmitted by the user terminal may further include exposure time information on a time during which the user is exposed to the specific location, and the health care server may generate the analysis information using the air quality information, the user location information, and the exposure time information.

The health care server may include: a health care controller configured to provide the treatment information using the analysis information analyzed from the air quality information, the user location information, and the exposure time information; and a database (DB) unit configured to store the air quality information, the user identification information, the user location information, and the exposure time information.

Here, the health care controller may include: a communication module configured to receive the air quality information, the user identification information, the user location information, and the exposure time information; an analysis module configured to analyze the air quality information, the user location information, and the exposure time information to generate analysis information on the user's respiratory status; and a treatment information generating module configured to generate treatment information on the user's respiratory system using the analysis information.

The DB unit may include a user identification information DB configured to store the user identification information; a user location information DB configured to store the user location information and the exposure time information; a user treatment history information DB configured to store user treatment history information on the user's respiratory system; and an air quality information DB configured to store the air quality information.

The user identification information may include at least an ID of the user for identifying the user, and when the user terminal is first registered in the health care server, the user terminal may transmit at least one of the user ID, the user's name, the user's age, and the user's gender to the health care server.

In addition, when the user terminal is first registered in the health care server, the user terminal may further transmit questionnaire information on the user's respiratory status and past treatment history of the user's respiratory system performed prior to registration to the health care server to the health care server and the health care server may update the user treatment history information with the questionnaire information and the past treatment history information.

The questionnaire information may include at least one of an occurrence time of dyspnea, the degree of dyspnea, a duration of dyspnea, a cause of respiratory disease, or a respiratory volume.

The health care server may generate the analysis information using the air quality information, the user location information, the exposure time information, and the user treatment history information.

The user terminal may transmit current status information on the user's respiratory status to the health care server.

The current status information may include (1) questionnaire information on the current user's respiratory status, (2) user image information obtained by imaging at least one of the current user's oral cavity, nasal cavity, eyes, ear canal, or skin, or (3) the current user's respiratory volume.

The health care server may update the user treatment history information with the current status information provided from the user terminal and generate the analysis information using the air quality information, the user location information, the exposure time information, the user treatment history information, and the current status information.

The health care server may further include a remote diagnosis module configured to provide at least one of the air quality information, the user identification information, the user location information, the exposure time information, the user treatment history information, and the current status information to an external source and to receive analysis information analyzed by the external source using the at least one information.

In addition, the health care system may further include: a complex treatment device capable of performing a respiratory treatment on at least one of the user's ear canal, oral cavity, eyes, or nasal cavity by interworking with the user terminal or the health care server, wherein the user terminal may have a health care application program linked with the complex treatment device.

The complex treatment device may include a main body capable of communicating with the user terminal and a treatment instrument capable of communicating with the main body or the user terminal and performing a respiratory treatment on at least one of the user's ear canal, oral cavity, eyes, or nasal cavity.

The treatment instrument may include at least one of a nebulizer, an injector, a low-power light irradiator, and an inhaler.

The health care server may provide the treatment information differentiated using at least one of the air quality information, the exposure time information, the user treatment history information, or the current status information included in the analysis information, and in the treatment information, information on a usage time or the number of times of use of at least one of the nebulizer, the injector, the low-power light irradiator, and the inhaler included in the complex treatment device may be provided to be different according to the at least one information.

The treatment information may be provided in at least one of forms of (1) message information or voice information output through the health care application program of the user terminal, (2) image or video information displayed through the health care application program of the user terminal, and (3) a treatment instrument control signal for controlling the complex treatment device through the health care application program of the user terminal.

When the user performs an operation of the complex treatment device according to the treatment information, the complex treatment device may transmit feedback information on an operation result of the complex treatment device to the user terminal.

The feedback information may include at least one of a coupling completion signal when the treatment instrument is inserted into the main body, an operation time and operation end signal for operating the treatment instrument, and a removal completion signal when the treatment instrument is separated from the main body.

The user terminal may transmit the feedback information to the health care server, and the health care server may update the user treatment history information with the feedback information.

The health care server may provide the treatment information in the form of a treatment instrument control signal to the user terminal, the user terminal may transmit the treatment instrument control signal to the complex treatment device according to the treatment information, and the complex treatment device may transmit the feedback information to the user terminal after an operation according to the treatment instrument control signal is completed.

In another aspect, a health care server for providing respiratory treatment information using air quality information, includes: a database (DB) unit configured to receive and store air quality information on at least one specific location inside or outside a building where a user is located, user identification information for identifying the user, and user location information; and a health care controller configured to receive the air quality information, the user identification information, and the user location information and to provide treatment information for the user's respiratory system using analysis information analyzed from the air quality information of an area where the user is located.

The air quality information may include indoor air quality information on at least one of a fine dust concentration, an ultra fine dust concentration, an indoor temperature, an indoor humidity, an oxygen concentration, a carbon dioxide concentration, a nitrogen oxide concentration, a formaldehyde concentration, a benzene concentration, a toluene concentration, an alcohol concentration, a methane gas concentration, a cigarette smoke concentration, and radon; and outdoor air quality information on at least one of an outdoor temperature, an outdoor humidity, a fine dust concentration, an ultrafine dust concentration, the degree of an ultraviolet ray, an outdoor air quality index, and a concentration of a criteria air pollutant.

The outdoor air quality index may be an integrated atmospheric environment index, and the criteria air pollutant may include at least one of $SO_2$, $CO$, $O_3$, and $NO_2$.

The user location information may further include exposure time information on a time during which the user is exposed to the specific location, and the health care controller may generate the analysis information using the air quality information, the user location information, and the exposure time information.

The health care controller may include: a communication module configured to receive the air quality information, the user identification information, the user location information, and the exposure time information; an analysis module configured to analyze the air quality information, the user location information, and the exposure time information to generate analysis information on the user's respiratory status; and a treatment information generating module configured to generate treatment information on the user's respiratory system using the analysis information.

The DB unit may include a user identification information DB configured to store the user identification information; a user location information DB configured to store the user location information and the exposure time information; a user treatment history information DB configured to store user treatment history information on the user's respiratory system; and an air quality information DB configured to store the air quality information.

The user identification information may include at least one of the user's ID, the user's name, the user's age, and the user's gender for identifying the user.

The health care controller may further receive initial questionnaire information on the user's respiratory status and past treatment history for the user's respiratory system performed prior to registration to the health care server and update the questionnaire information and the past treatment history information to the DB unit.

The questionnaire information may include at least one of an occurrence time of dyspnea, the degree of dyspnea, a duration of dyspnea, a cause of respiratory disease, or a respiratory volume.

The health care controller may generate the analysis information using the air quality information, the user location information, the exposure time information, and the user treatment history information.

The health care controller may receive current status information on the user's respiratory status.

The current status information may include (1) questionnaire information on the current user's respiratory status, (2) user image information obtained by imaging at least one of the current user's oral, nasal, eye, ear canal, or skin, or (3) the current user's respiratory volume.

The health care controller may update the current status information provided from the user terminal to the DB unit and generate the analysis information using the air quality information, the user location information, the exposure time information, the user treatment history information, and the current status information.

The health care controller may further include a remote diagnosis module configured to provide at least one of the air quality information, the user identification information, the user location information, the exposure time information, the user treatment history information, and the current status information to an external source and to receive analysis information analyzed by the external source using the at least one information.

The health care controller may provide the treatment information differentiated using at least one of the air quality information, the exposure time information, the user treatment history information, or the current status information included in the analysis information, and in the treatment information, information on a usage time or the number of times of use of at least one of treatment instruments among a nebulizer, an injector, a low-power light irradiator, and an inhaler may be different for each treatment instrument.

The treatment information may be provided in at least one of (1) a form of message information or voice information, (2) a form of image or video information, and (3) a form of a treatment instrument control signal for controlling a complex treatment device.

The health care controller may receive feedback information on an operation result of the complex treatment device after the complex treatment device completes the operation according to the treatment information.

The feedback information may include at least one of a coupling completion signal when the treatment instrument is inserted into the main body, an operation time and operation end signal for operating the treatment instrument, and a removal completion signal when the treatment instrument is separated from the main body.

The health care controller may update the feedback information to the DB unit.

The health care controller may provide the treatment information in the form of a treatment instrument control signal, and after the complex treatment device completes an operation according to the treatment instrument control signal, the health care controller may receive feedback information on the treatment instrument control signal from the complex treatment device.

In another aspect, a health care method for providing respiratory treatment information using air quality information, includes: receiving, by a health care server, air quality information on at least one specific location inside or outside a building where a user is located, user identification information for identifying the user, and user location information; and receiving, by the health care server, the air quality information, the user identification information, and the user location information and providing treatment information on the user's respiratory system using analysis information analyzed from the air quality information of an area where the user is located.

The air quality information may include indoor air quality information on at least one of a fine dust concentration, an ultra fine dust concentration, an indoor temperature, an indoor humidity, an oxygen concentration, a carbon dioxide concentration, a nitrogen oxide concentration, a formaldehyde concentration, a benzene concentration, a toluene concentration, an alcohol concentration, a methane gas concentration, a cigarette smoke concentration, and radon; and outdoor air quality information on at least one of an outdoor temperature, an outdoor humidity, a fine dust concentration, an ultrafine dust concentration, the degree of an ultraviolet ray, an outdoor air quality index, and a concentration of a criteria air pollutant.

The outdoor air quality index may be an integrated atmospheric environment index, and the criteria air pollutant may include at least one of $SO_2$, $CO$, $O_3$, and $NO_2$.

The user location information may further include exposure time information regarding a time during which the user is exposed to the specific location.

The health care server may generate the analysis information using the air quality information, the user location information, and the exposure time information.

The user identification information may include at least one of the user's ID, the user's name, the user's age, and the user's gender for identifying the user.

The health care server may further receive initial questionnaire information on the user's respiratory status and past treatment history regarding the user's respiratory system performed prior to registration to the health care server and store and update the questionnaire information and the past treatment history information as user treatment history information.

The questionnaire information may include at least one of an occurrence time of dyspnea, the degree of dyspnea, a duration of dyspnea, a cause of respiratory disease, or a respiratory volume.

The health care server may generate the analysis information using the air quality information, the user location information, the exposure time information, and the user treatment history information.

The health care server may further receive current status information on the user's respiratory status.

The current status information may include (1) questionnaire information on the current user's respiratory status, (2) user image information obtained by imaging at least one of the current user's oral cavity, nasal cavity, ear canal, eyes, or skin, or (3) the current user's respiratory volume.

The health care server may store the current status information and generate analysis information using the air quality information, the user location information, the exposure time information, the user treatment history information, and the current status information.

The health care server may provide at least one of the air quality information, the user identification information, the user location information, the exposure time information, the user treatment history information, and the current status information to an external source and receive analysis information analyzed by the external source using the at least one information.

The health care server may provide the treatment information differentiated using at least one of the air quality information, the exposure time information, the user treatment history information, or the current status information included in the analysis information, and in the treatment information, information on a usage time or the number of times of use of at least one of treatment instruments among a nebulizer, an injector, a low-power light irradiator, and an inhaler may be different for each treatment instrument.

The treatment information may be provided in at least one of (1) a form of message information or voice information, (2) a form of image or video information, and (3) a form of a treatment instrument control signal for controlling a complex treatment device.

The health care server may receive feedback information on an operation result of the complex treatment device after the complex treatment device completes the operation according to the treatment information.

The feedback information may include at least one of a coupling completion signal when the treatment instrument is inserted into the main body, an operation time and operation end signal for operating the treatment instrument, and a removal completion signal when the treatment instrument is separated from the main body.

The health care server may provide the treatment information in the form of a treatment instrument control signal, and after the complex treatment device completes an operation according to the treatment instrument control signal, the health care server may receive feedback information on the treatment instrument control signal from the complex treatment device.

Advantageous Effects

In the health care system, the health care server, and the health care method for providing respiratory treatment information using air quality information according to examples of the present disclosure, since the health care server provides treatment information on the user's respiratory system analyzed and processed from air quality information on a specific location, which is an area or space in which the user is located, the user may more conveniently treat and manage his or her respiratory system.

DESCRIPTION OF DRAWINGS

FIG. 12 is a view illustrating a first embodiment of treatment information provided by the health care server 100 according to the present disclosure.

FIG. 13 is a view illustrating a second embodiment of treatment information provided by the health care server 100 according to the present disclosure.

FIG. 14 is a view illustrating a third embodiment of treatment information provided by the health care server 100 according to the present disclosure.

FIG. 15 is a view illustrating a form of treatment information provided by the health care server 100 according to an example of the present disclosure.

BEST MODES

Hereinafter, embodiments of the present disclosure will be described in detail with reference to the accompanying drawings. In describing the present invention, if it is determined that a detailed description of known functions and components associated with the present invention unnecessarily obscure the gist of the present invention, the detailed description thereof will be omitted. The terms used henceforth are used to appropriately express the embodiments of the present invention and may be altered according to a person of a related field or conventional practice. Therefore, the terms should be defined on the basis of the entire content of this specification.

Hereinafter, a health care system, a health care server 100, and a health care method according to an example of the present disclosure will be described with reference to the accompanying drawings.

Figure 1:
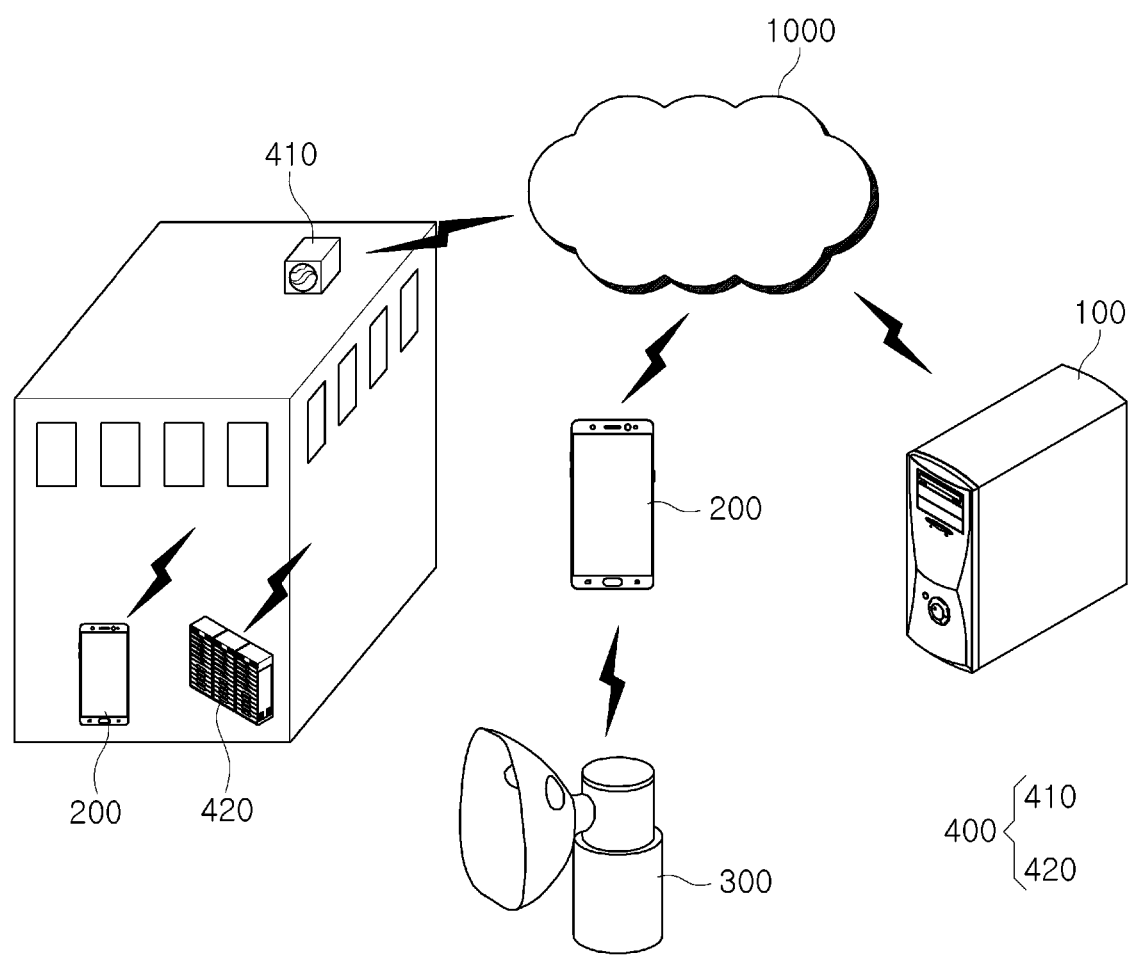
FIG. 1 is a view illustrating a concept of a health care system according to an example of the present disclosure.
Figure 2:
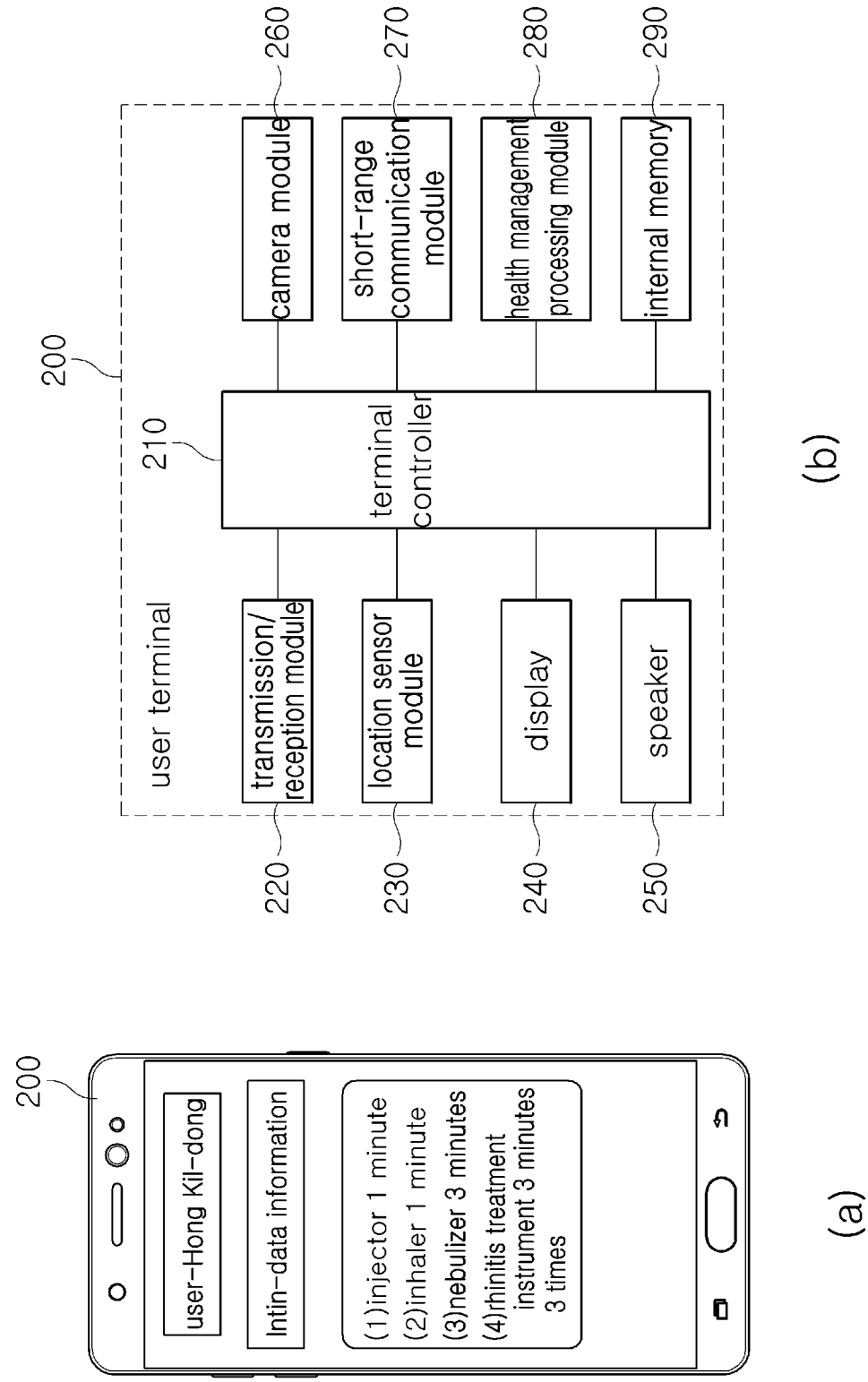
FIG. 2 is a view illustrating an example of a user terminal 200 in FIG. 1.
Figure 3:
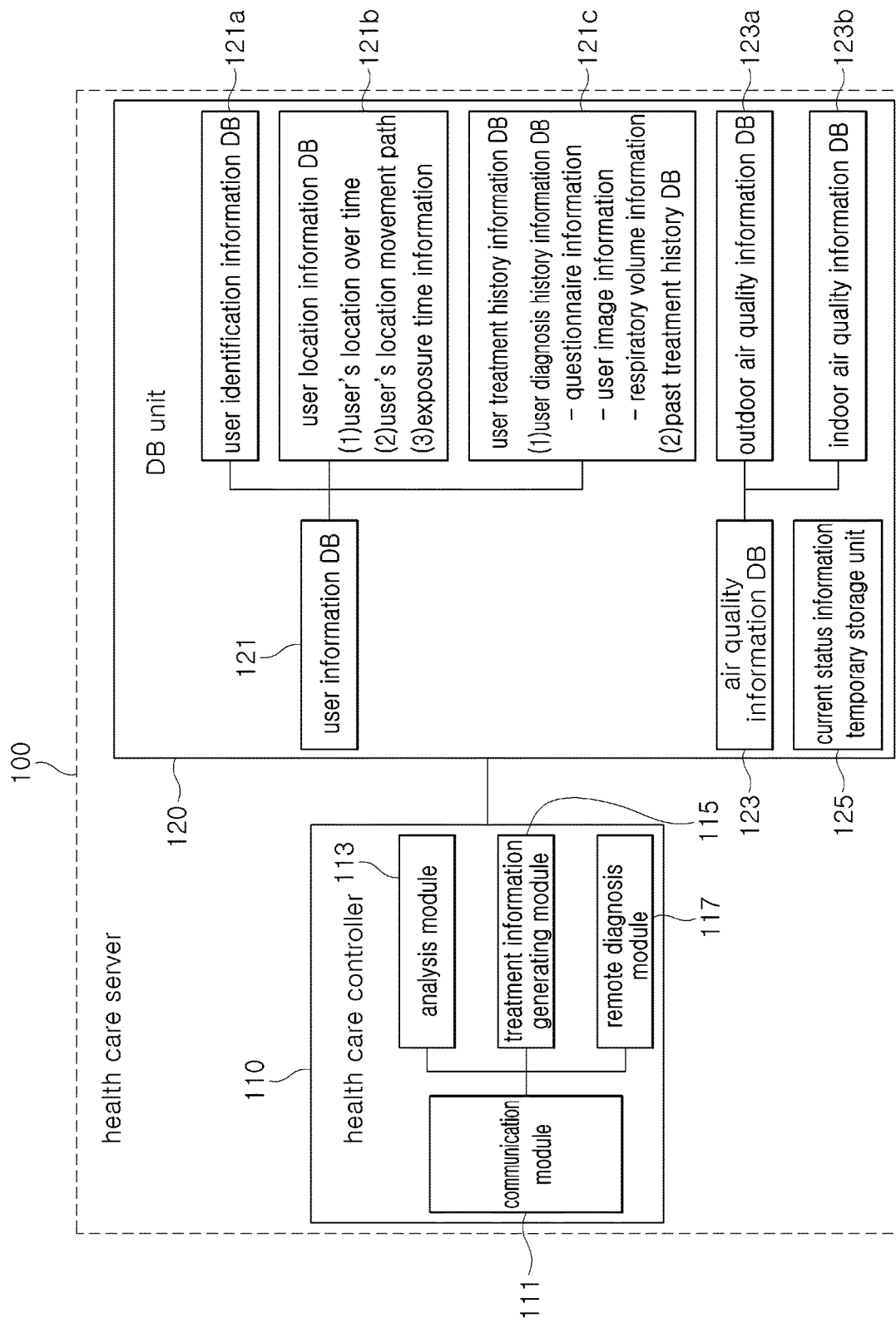
FIG. 3 is a view illustrating an example of a health care server 100 in FIG. 1.
Figure 4:
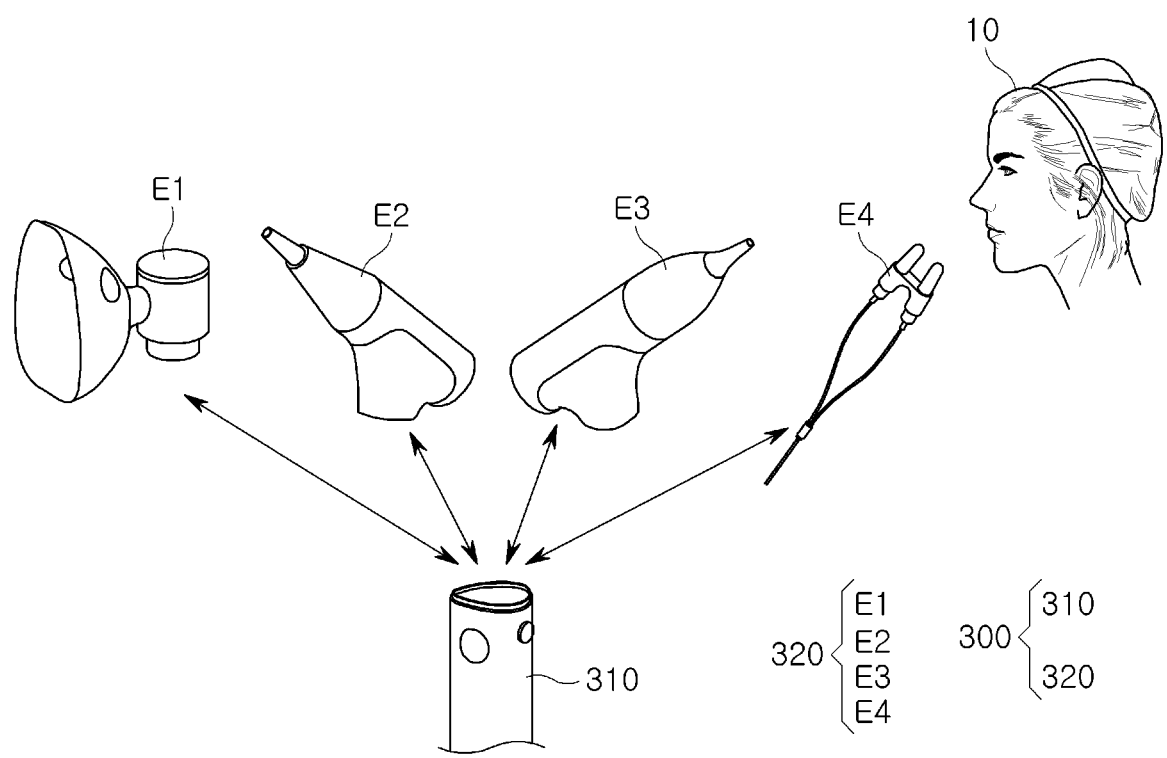
FIG. 4 is a view illustrating an example of a complex treatment device 300 in FIG. 1.
Figure 5:
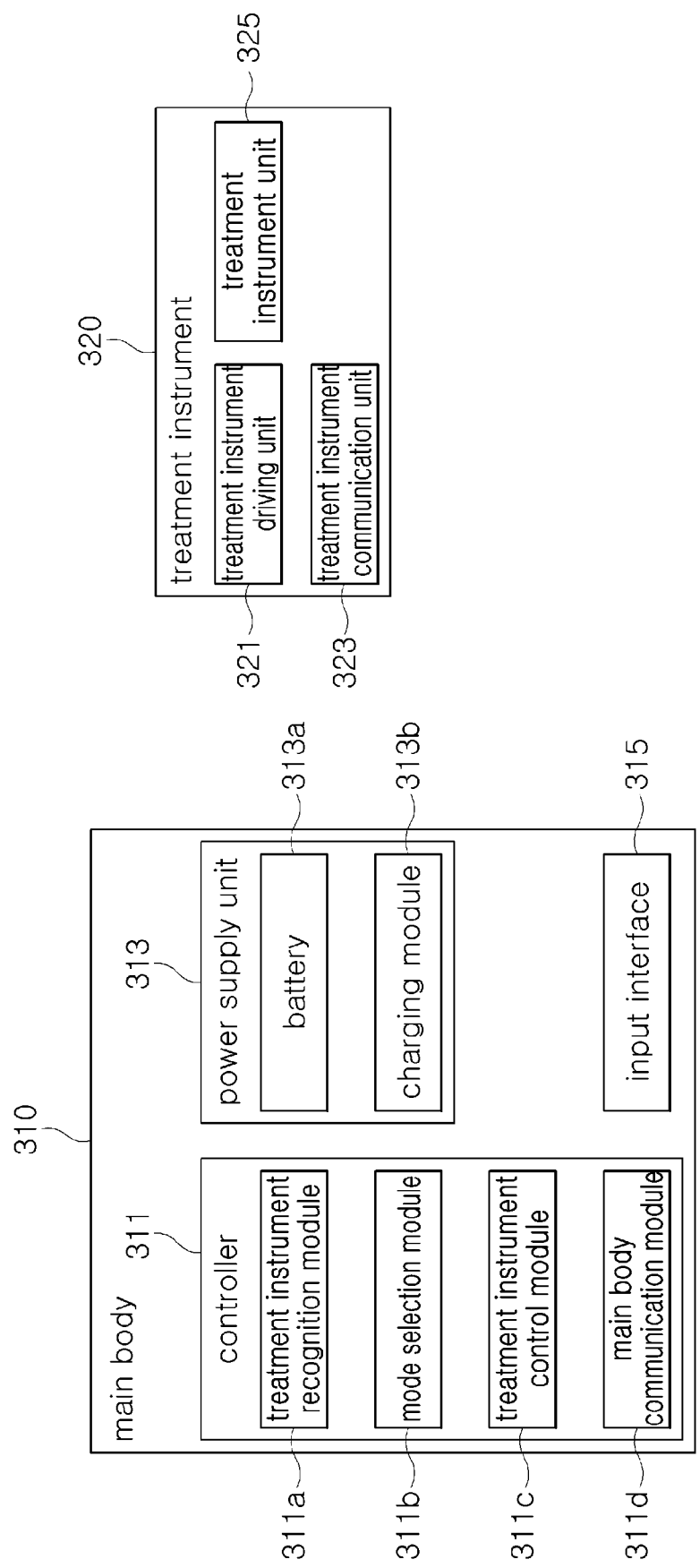
FIG. 5 is a view illustrating a configuration of a main body 310 and a treatment instrument 320 shown in FIG. 4.

FIG. 1 is a view illustrating a concept of a health care system according to an example of the present disclosure, FIG. 2 is a view illustrating an example of a user terminal 200 in FIG. 1, FIG. 3 is a view illustrating an example of a health care server 100 in FIG. 1, FIG. 4 is a view illustrating an example of a complex treatment device 300 in FIG. 1, and FIG. 5 is a view illustrating a configuration of a main body 310 and a treatment instrument 320 shown in FIG. 4.

As shown in FIG. 1, a health care system according to an example of the present disclosure may include a health care server 100, a user terminal 200, a complex treatment device 300, and an air quality measurement unit 400.

The air quality measurement unit 400 may be located in at least one of the inside or outside of the building and may transmit air quality information on a corresponding area or a corresponding space to the health care server 100.

The user terminal 200 may transmit user identification information for identifying a user and user location information on a specific location in which the user is located to the health care server 100.

The health care server 100 may receive the air quality information, the user identification information, and the user location information and provide treatment information for a user's respiratory system using analysis information analyzed from the air quality information in the area where the user is located.

The complex treatment device 300 may include a treatment instrument 320 capable of performing various treatments on the user's respiratory system. When the user uses the complex treatment device 300, the complex treatment device 300 may interwork with the user terminal 200 to transmit feedback information regarding an operation and use of the complex treatment device 300 to the user terminal 200.

The health care system described above will be described in more detail as follows.

The air quality measurement unit 400 may be located inside or outside the building and may transmit the air quality information on a specific location in which the user is located to the health care server 100.

The air quality information provided by the air quality measurement unit 400 (1) may be linked with the air quality measurement unit 400 and transmitted to the health care server 100 through a communication network such as an Internet communication network 1000 or (2) may be transmitted from the air quality measurement unit 400 to the user terminal 200 through a short-range communication network and the user terminal 200 may transmit the air quality information to the health care server 100.

The air quality measurement unit 400 may include an indoor air quality measurer 420 and an outdoor air quality measurer 410. When each of the indoor air quality measurer 420 and the outdoor air quality measurer 410 transmits THE air quality information to the health care server 100, location information of the measurer in which the air quality measurer is currently located may be transmitted together.

To this end, each of the indoor air quality measurer 420 and the outdoor air quality measurer 410 may include a measurement unit for measuring various air quality and a communication unit communicating with the user terminal 200 or the health care server 100.

The indoor air quality measurer 420 may be located in a building at a short distance adjacent to the user and may measure indoor air quality inside the building to generate indoor air quality information.

The indoor air quality information measured by the indoor air quality measurer 420 may be transmitted to the user terminal 200 through a short-range communication network such as a Wi-Fi communication network or a Bluetooth communication network, for example, and the user terminal 200 may transmit the indoor air quality information to the health measurement device through the Internet communication network 1000. However, the present disclosure is not limited thereto and the indoor air quality measurement unit 400 may transmit the indoor air quality information to the health care server 100 through a communication network such as the Internet communication network 1000 without passing through the user terminal 200.

Such indoor air quality information may include at least one of, for example, an indoor fine dust concentration, an indoor ultrafine dust concentration, an indoor temperature, indoor humidity, an oxygen concentration, a carbon dioxide concentration, a nitrogen oxide concentration, a formaldehyde concentration, a benzene concentration, a toluene concentration, an alcohol concentration, a methane gas concentration, a cigarette smoke concentration, and radon.

In addition, the indoor air quality measurer 420 may have a built-in micro sensor that may detect indoor sound. Accordingly, when the indoor air quality measurer 420 is located in a residential space, the number of coughs of a user located in the residential space may be measured. In addition, the indoor air quality measurer 420 may measure the number of coughs of the user by time and transmit the same to the health care server 100. Accordingly, the health care server 100 may obtain information on the number of coughs of the user living in the corresponding residential space by time and recognize how many the number of coughs of the user has increased in the evening or night time as compared to a daytime.

The outdoor air quality measurer 410 may be located at a distance from the user, may be provided outside the building, and may measure outdoor air quality information. The measured outdoor air quality information may be transmitted to the health care server 100 through a communication network such as the Internet communication network 1000 linked to the outdoor air quality measurer 410.

The outdoor air quality information measured by the outdoor air quality measurer 410 may include outdoor air quality information on at least one of an outdoor temperature, an outdoor fine dust concentration, an outdoor ultrafine dust concentration, the degree of ultraviolet (UV) light, an outdoor air quality index, and a concentration of a criteria air pollutant. Here, the outdoor air quality index may be an integrated atmospheric environment index, and the criteria air pollutant may include at least one of $SO_2$, CO, $O_3$, and $NO_2$.

Such outdoor air quality information is information provided from a measurer installed outdoors for the purpose of public use and may be information provided by the Meteorological Agency, a public institution, or information provided by a private company for public use.

The user terminal 200 may transmit user identification information for identifying the user and user location information on a specific location in which the user is located to the health care server 100.

To this end, the user terminal 200 may be provided in the form of a mobile phone or a smartphone and a wireless communication terminal that the user may carry around, for example, as shown in FIG. 2A.

However, the present disclosure is not limited thereto and may include any wired or wireless communication device as long as it is communicatable. As an example, the user terminal 200 according to the present disclosure may include a wearable device including a mobile phone, a smartphone, a tablet computer, a laptop computer, a portable media player, a personal digital assistant (PDA), a smart watch, or smart glasses enabling wireless communication, a navigation device, and the like.

As shown in (b) of FIG. 2, the user terminal 200 may include a terminal controller 210, a transceiver module 220, a position sensor module 230, a display unit 240, a speaker 250, and a camera module. 260, a short-range communication module 270, a health care processing module 280, an internal memory 290, and may include various general functional modules performing a call function for performing a function of a mobile phone or a smartphone and a wireless communication terminal, a message transmission function, an input interface 315 function, and the like.

The terminal controller 210 may control various functions processed in the user terminal 200 by interworking with the transceiver module 220, the position sensor module 230, the display unit 240, the speaker 250, the camera module 260, the short-range communication module 270, the health care processing module 280, and the internal memory 290. For example, when indoor air quality information is transmitted from the indoor air quality measurer, the terminal controller 210 may transmit the indoor air quality information to the health care server 100, or when the user terminal 200 transmits user identification information and user location information to the health care server 100, the terminal controller 210 may control the user terminal 200.

In addition, when the user terminal 200 exchanges related information with the health care server 100, the user terminal 200 may transmit or receive information under the control of the terminal controller 210, and when the user performs a desired operation through the user terminal, the corresponding operation or function may be controlled through the terminal controller 210.

The transceiver module 220 may be used when the user terminal 200 transmits air quality information, user location information, or user identification information through the Internet, or may perform a function of receiving treatment information from the health care server 100. In addition, the transceiver module 220 may perform a function of transmitting or receiving corresponding information when exchanging various information with the health care server 100.

The location sensor module 230 may detect a current location of the user terminal 200 and generate user location information on where the user is currently located. Such a position sensor module 230 may be, for example, a global positioning system (GPS) device.

The display unit 240 may perform a function of displaying the treatment information transmitted from the health care server 100 on the user terminal 200 as shown in (a) of FIG. 2B. In addition, when the user inputs questionnaire information through the user terminal 200, a response regarding a question of the given questionnaire information may be input through the input interface 315 built in the display unit 240. When registering to the health care server 100 for the first time, various user information may be input through the input interface 315 built in the display unit 240.

When voice information is included in the treatment information transmitted from the health care server 100 to the user terminal 200, the speaker 250 may output the corresponding voice information in the form of sound.

The camera module 260 may image at least one of an oral cavity, a nasal cavity, an ear canal, eyes, or skin by interworking with an otoscope, parenteral or endoscope is used when photographing at least one of the user's oral cavity, nasal cavity, external ear canal, eyes, or skin, and is interlocked with an otoscope, a rhinoscope or an endoscope that may be used to image at least one of the oral cavity, nasal cavity, ear canal, eyes, or skin.

The short-range communication module 270 may perform a communication function when exchanging various information with the indoor air quality measurer 420 or the complex processing module and may be provided in the form of a Wi-Fi device or a Bluetooth device.

The internal memory 290 may store the user identification information, the user location information, and the indoor air quality information transmitted from the indoor air quality measurer 420.

The health care processing module 280 may be provided in the form of a health care application program. The user may operate the health care processing module 280 to access the health care server 100 or interwork with the complex processing module.

As an example, when the user operates the health care processing module 280 to execute the health care application program, the user terminal 200 may transmit user location information to the health care server 100 and may receive treatment information from the health care server 100.

More specifically, when the user is located outdoors outside the building and operates the health care processing module 280 to run the health care application program, user location information of the user located outdoors may be transmitted to the health care server 100, and the health care server 100 may be provided with outdoor air quality information from the outdoor air quality measurer 410 in an area where the user is located, analyze the outdoor air quality information, and provide treatment information to the user terminal 200. The user may check the treatment information through the health care processing module 280.

Alternatively, when the user is located indoors inside the building and operates the health care processing module 280 to run the health care application program, the user terminal 200 transmits user location information of the user located indoors to the health care server 100, and the health care server 100 may receive indoor air quality information from the indoor air quality measurer 420 in the area where the user is located through the Internet communication network 1000 or the user terminal 200, analyze the indoor air quality information, and provide treatment information to the user terminal 200.

Here, the user location information transmitted from the user terminal 200 may further include exposure time information regarding a time during which the user is exposed to a specific location.

Accordingly, the health care server 100 may check how long the user has stayed at the specific location based on the exposure time information and may provide treatment information differentiated according to the exposure time information to the user through the exposure time information of the user.

The user identification information transmitted by the user terminal 200 to the health care server 100 may include an ID of the user for identifying the user, and such user identification information may be transmitted to the health care server 100 when the user is first registered to the health care server 100.

As an example, when the user accesses the health care server 100 through the user terminal 200, the health care server 100 may request at least one of a user ID, the user's name, the user's age, and the user's gender from the user terminal 200 to identify the user, and the user terminal 200 may transmit the requested item to the health care server 100.

In addition, in order to verify basic information on the user's respiratory status, the health care server 100 may request initial questionnaire information on the user's respiratory status and past treatment history on the user's respiratory system performed prior to registration to the health care server 100 from the user through the user terminal 200 and may receive the requested item through the user terminal 200.

When the initial questionnaire information and the past treatment history information on the user's respiratory system is received, the health care server 100 may store the initial questionnaire information and the past treatment history information, as user treatment history information on the user's respiratory system in a DB unit 120 linked to the health care server 100 by users and perform updating.

The initial questionnaire information may include at least one of an occurrence time of dyspnea, the degree of dyspnea, a duration of dyspnea, a cause of respiratory disease, or a respiratory volume. The respiration volume may include one of an exhalation volume, which is an amount exhaled by the user, and an inhalation volume that the user breathes in.

In addition, the user terminal 200 may further transmit current status information on the user's respiratory status to the health care server 100.

The current status information is information from which the current user's status is known and may include (1) questionnaire information on the current user's respiratory status, (2) user image information obtained by imaging at least one of the current user's oral cavity, nasal cavity, ear canal, eyes, or skin, or (3) the current user's respiratory volume.

Here, (1) the current questionnaire information on the current user's respiratory status may include an occurrence time of dyspnea of the current user, the degree of dyspnea, a duration of dyspnea, a time of the last drug injection related to the respiratory system, a drug dose, the user's current physical condition, sleep time, and the like. The current questionnaire information may be input through the user terminal after the user operates the health care application program through the user terminal 200, and may be transmitted to the health care server 100.

(2) The user image information on the current user's respiratory status may be image information captured and obtained by the user using the user terminal 200 or may be linked to the user terminal 200 and obtained by imaging the user's oral cavity, nasal cavity, ear canal, eyes, or skin.

Such image information may be obtained by the user terminal 200 using an otoscope, an ophthalmoscope, a rhinoscope, an endoscope, or the like which is capable of imaging and linked to the user terminal 200.

(3) The current user's respiration volume information may be acquired by the user terminal 200 by a respiration volume measurer linked with the user terminal 200 and worn on the user's mouth to measure the user's inhalation volume or exhalation volume.

Here, specifically, the user's respiratory volume information may include information on a component and a concentration of at least one of a carbon dioxide concentration, a hydrogen sulfide concentration, a moisture concentration, and a nitric oxide contained in the user's breath at the time of exhalation that the user breathes out.

The current status information may further include the user's main body temperature information measured by a thermometer and obtained by the user terminal 200 in addition to at least one of the aforementioned (1) current questionnaire information, (2) image information, and (3) respiratory volume information.

In this manner, the current status information on the user's respiratory status acquired by the user terminal 200 may be transmitted to the health care server 100 and stored, and may be updated in the user's treatment history information.

In addition, the user terminal 200 may operate the complex treatment device 300 according to the treatment information provided from the health care server 100 and transmit feedback information provided from the complex treatment device 300 to the health care server 100.

The health care server 100 may be linked with the air quality measurement unit 400 and the user terminal 200, may receive air quality information from the air quality measurement unit 400, and may receive at least user identification information and user location information from the user terminal 200.

To this end, the health care server 100 may include a health care controller 110 and a database (DB) unit 120.

The health care controller 110 may provide treatment information to the user terminal 200 using analysis information analyzed from the air quality information, the user location information, and the exposure time information.

However, the present disclosure is not limited thereto, and the health care controller 110 may provide treatment information using the analysis information analyzed using the user treatment history information on the user's respiratory system in addition to the air quality information, the user location information, and the exposure time information or may provide treatment information using the analysis information analyzed using the current status information on the user's current respiratory system.

To this end, the health care controller 110 may include a communication module 111, an analysis module 113, a treatment information generating module 115, and a remote diagnosis module 117.

The communication module 111 may function to link the user terminal 200 to the health care server 100 and the air quality measurer to the health care server 100 through the Internet communication network 1000, receive information (e.g., indoor air quality information, user identification information, user location information, current status information, and feedback information, etc.) transmitted from the user terminal 200 to the health care server 100, transmit information from the health care server 100 to the user terminal 200, and receive outdoor air quality information transmitted from the outdoor air quality measurer 410.

The analysis module 113 may generate analysis information upon receiving the air quality information, the user identification information, the user location information, and the exposure time information.

Here, the analysis information may be data information obtained by estimating or diagnosing the user's current respiratory status by analyzing the air quality information, the user identification information, the user location information, and the exposure time information.

Therefore, the analysis information may estimate or diagnose the current status of the user's respiratory system according to the degree of data provided as a factor of the analysis information, and as the type or amount of the data provided as a factor of the analysis information increases, the current status of the user's respiratory system may be more accurately analyzed.

When the air quality information, the user identification information, and the exposure time information are provided to the analysis module 113, the analysis module 113 may generate analysis information estimated for the current status of the user's respiratory system, and when the user treatment history information, in addition to the air quality information, the user identification information, and the exposure time information, is provided to the analysis module 113, the analysis module 113 may generate analysis information by including the user treatment history information in an analysis basis.

In addition, when even the current status information, in addition to the air quality information, the user identification information, and the exposure time information, and the user treatment history information, is provided to the analysis module 113, the analysis module 113 may generate analysis information by including even the current status information on the user's respiratory system in the analysis basis.

The treatment information generating module 115 may generate treatment information using analysis information generated from the analysis information. The treatment information generating module 115 may generate, as treatment information, contents that may use a type of treatment instrument 320 provided in the complex treatment device 300 linked to the user terminal 200.

The remote diagnosis module 117 may visualize the air quality information, the user treatment history information, and the current status information transmitted to the health care server 100 in the form of a document, image or table for easy viewing by experts, provide the same to an external source, and receive analysis information from the external source. The treatment information generating module 115 may generate treatment information based on the analysis information provided from the external source.

The DB unit 120 may store the air quality information, the user identification information, the user location information including the exposure time information, the user treatment history information, and the current status information transmitted to the health care server 100.

To this end, the DB unit 120 may include a user information DB 121, an air quality information DB 123, and a current status information temporary storage unit 125.

In addition, FIG. 3 illustrates a case where the DB unit 120 is included in the health care server 100 as an example, but the DB unit 120 may not be included in the health care server 100 and may be separately managed in a separate space. However, hereinafter, for convenience of description, a case where the DB unit 120 is included in the health care server 100 will be described as an example.

The user information DB 121 may include a user identification information DB 121*a*, a user location information DB 121*b*, and a user treatment history information DB 121*c*.

The user identification information DB 121*a* may store information on at least one of the user ID, the user's name, the user's age, and the user's gender transmitted when the user terminal 200 registers to the health care server 100. If the user's age is lower than a preset reference, the user identification information DB 121*a* may separately store information on at least one of IDs, names, ages, and genders of the user's parents linked with the user ID.

The user location information DB 121*b* may classify the user location information provided from the user terminal 200 into the user's location over time, the user's location movement path, and exposure time information at each specific location, and stores and updates the same.

The user treatment history information DB 121*c* may store initial questionnaire information transmitted when the user terminal 200 registers to the health care server 100 and past treatment history of the user's respiratory system performed prior to registration to the health care server 100, and store questionnaire information on the current user's respiratory status transmitted for the user to receive treatment information, user image information on the user's respiratory system, and respiratory volume information on the user's current respiratory volume.

To this end, the user treatment history information DB 121*c* may include a user's diagnosis history information DB and a past treatment history DB.

The user's diagnosis history information DB may classify the information on the user's respiratory system transmitted from the user terminal 200 into initial questionnaire information, current questionnaire information, user image information, and respiratory volume information, and store the same.

The past treatment history DB may store the past treatment history regarding the user's respiratory system, and after the user is registered to the health care server 100, the past treatment history DB may receive treatment information and store feedback information of the complex treatment device 300 transmitted through the user terminal 200.

The air quality information DB 123 may include an outdoor air quality information DB 123*a* and an indoor air quality information DB 123*b*.

The outdoor air quality information DB 123*a* may store and update the outdoor air quality information transmitted from the outdoor air quality measurer 410 in time order, and the indoor air quality information DB 123*b* may store and update indoor air quality information transmitted from the indoor air quality measurer 420 in time order.

The current status information temporary storage unit 125 may temporarily store current status information including at least one of the questionnaire information, the user image information, or the respiratory volume information indicating the current status of the user transmitted from the user terminal 200. The health care controller 110 may perform analysis using the current status information stored in the temporary storage unit, provide treatment information to the user terminal 200, and update the current status information to the user treatment history information DB 121*c*.

The complex treatment device 300 may be operated in conjunction with the health care processing module 280 of the user terminal 200 and may perform a respiratory treatment on at least one of the user's ear canal, oral cavity, eyes, or nasal cavity.

For example, the complex treatment device 300 may perform treatment on the user's ear (otology), nose (rhinology), throat (pharyngeal/larynx, head and neck surgery), and eyes (ophthalmology).

As shown in FIG. 4, the complex treatment device 300 may include a main body 310 which is communicatable with the user terminal 200 and a treatment machine 320 communicatable with the main body 310 or the user terminal 200 and performs a respiratory treatment on at least one of the user's ear canal, oral cavity, eyes, or nasal cavity.

Here, as an example, the treatment instrument 320 may include at least one of a nebulizer E1, an injector E2, an inhaler E3, and a low-power light irradiator E4.

Here, the low-power light irradiator E4 is described as a rhinitis treatment instrument E4 for the purpose of treating rhinitis, for example, but the present disclosure is not limited thereto and the low-power light irradiator E4 may also be used for treatment of the eyes, ear canal, etc.

Hereinafter, for convenience of explanation, a case where the low-power light irradiator E4 is the rhinitis treatment instrument E4 will be described as an example.

The nebulizer E1 may treat the user's nasal cavity or oral cavity by generating a mist containing a drug, and the injector E2 may inject a liquid or powdered drug or saline solution to the user's nasal cavity or oral cavity. The rhinitis treatment instrument E4 may be inserted into the user's nasal cavity and may irradiate the user's nasal cavity with a light source, and the inhaler E3 may be inserted into the user's nasal cavity and may function as a suction to inhale foreign substances in the nasal cavity.

In addition, in the present disclosure, a case where the treatment instrument 320 includes at least one of the nebulizer E1, the injector E2, the rhinitis treatment instrument E4, and the inhaler E3 has been described as an example, but, in addition, various other devices that may treat the user's respiratory system may be further included.

Each of the treatment instruments 320 such as the nebulizer E1, the injector E2, the rhinitis treatment instrument E4, and the inhaler E3 may be inserted and coupled to the main body 310 so as to be electrically connected to the main body 310.

In other words, the complex treatment apparatus 300 according to the present disclosure may include a plurality of treatment instruments 320 that may be coupled to one main body 310, and when each of the treatment instruments 320 is coupled to the main body 310, the main body 310 and the treatment instrument 320 may be electrically connected to each other and the treatment instrument 320 may be operated according to a control signal of the main body 310.

To this end, the main body 310 may include a controller 311, a power supply unit 313, and an input interface 315.

The controller 311 may include a treatment instrument recognition module 311*a*, a mode selection module 311*b*, a treatment instrument control module 311*c*, and a main body communication module 311*d*.

When the treatment instrument 320 is coupled to the main body 310, the treatment instrument recognition module 311*a* may recognize the treatment instrument 320 coupled to the main body 310. As an example, the treatment instrument recognition module 311*a* may receive a corresponding treatment instrument unique ID assigned to each treatment instrument 320 from the treatment instrument 320 coupled to the main body 310 and recognize the treatment instrument coupled to the main body 310 through the unique ID.

The mode selection module 311*b* may select an operation mode suitable for the treatment instrument 320 coupled to the main body 310. That is, when a certain treatment instrument 320 is coupled to the main body 310, the mode selection module 311*b* may select a mode appropriate for the corresponding treatment instrument 320 so that the main body 310 may output a corresponding treatment instrument control signal to the treatment instrument 310 according to the corresponding treatment instrument 320. For example, when the inhaler E3 having a suction function is coupled to the main body 310, the main body 310 may select a suction unit mode.

The treatment instrument control module 311*c* may output a control signal for operating the treatment instrument 320 coupled to the main body 310 according to the mode selected by the mode selection module 311*b* to the treatment instrument 320 to operate the treatment instrument 320.

The main body communication module 311*d* serves to allow the main body 310 to communicate with the user terminal 200, and when a control signal is transmitted from the user terminal 200 to the complex treatment device 300, the main body communication module 311*d* may receive the corresponding control signal.

The power supply unit 313 may include a battery 313*a* supplying power for the main body 310 and the treatment instrument 320 to operate and a charging module 313*b* for charging the battery 313*a* provided in the power supply unit 313 wirelessly or wiredly.

After the treatment instrument 320 is coupled to the main body 310 and the main body 310 recognizes the treatment instrument 320 and selects a mode for the treatment instrument 320, the input interface 315 may transmit a treatment control signal to the treatment instrument 310 so that the corresponding treatment instrument 320 may be turned on or turned off according to a user selection.

For example, when the treatment instrument control signal is not received from the user terminal 200 and the complex treatment device 300 is to be operated, the user may control the operation of the corresponding treatment instrument 320 by controlling the treatment instrument 320 coupled to the main body 310 to be turned on or turned off directly.

However, when the treatment instrument control signal is received from the user terminal 200, the treatment instrument control module 311*c* may output a control signal for the treatment instrument 320 to control the operation of the treatment instrument 320.

The treatment instrument 320 including at least one of the nebulizer E1, the injector E2, the rhinitis treatment instrument E4, and an inhaler E3 may include a treatment instrument driving unit 321, a treatment instrument communication unit 323, and a treatment instrument unit 325.

The treatment instrument communication unit 323 may interwork with the main body 310 or the user terminal 200 to transmit information on the operation of the treatment instrument driving unit 321 to the main body 310 or the user terminal 200.

The treatment instrument driving unit 321 may operate the treatment instrument unit 322 provided in the treatment instrument 320 according to a control signal for the treatment instrument 320 transmitted from the main body 310. For example, if the treatment instrument 320 coupled to the main body 310 is the rhinitis treatment instrument E4 having an LED light source device, the treatment instrument driving unit 321 may turn on the LED light source device, and if the treatment instrument 320 coupled to the main body 310 is the inhaler E3 including a compressor to perform a suction function, the treatment instrument driving unit 321 may operate the compressor according to a control signal for the treatment instrument 320 transmitted from the main body 310.

The treatment instrument 320 may include the treatment instrument unit 325 for performing each function of, for example, the nebulizer E1, the injector E2, the rhinitis treatment instrument E4, and the inhaler E3.

For example, in the case of the nebulizer E1, an ultrasonic generator or a motor for generating a mist containing a drug may be included in the treatment instrument unit 322, and in the case of the injector E2, a compressor for injecting a liquid, powdered drug, saline solution, or the like may be included in the treatment instrument unit 322.

In addition, in the case of the rhinitis treatment instrument E4, a light source for irradiating the user's nasal cavity with a light source, for example, a light emitting diode (LED), and a laser diode (LD) may be included in the treatment instrument unit 322. Here, a case where a low-power light irradiator is used as a rhinitis treatment instrument is described as an example so that the user's nasal cavity is irradiated with the light source, but the present disclosure is not limited thereto and the user's ear canal or eyes may be irradiated by the low-power light irradiator.

In the case of the inhaler E3, a compressor for inhaling foreign substances from the user's nasal cavity or oral cavity may be included in the treatment instrument unit 322.

Such a complex treatment device 300 provides treatment information from the health care server 100 to the user terminal 200 so that when the user operates the complex treatment device 300 according to the treatment information or when the complex treatment device 300 is operated according to a treatment instrument control signal for operating the complex treatment device 300 from the user terminal 200, the complex treatment device 300 may transmit feedback information which is a result value for the operation of the complex treatment device 300 to the user terminal.

Hereinafter, a method of operating the aforementioned health care system will be described.

Figure 6:
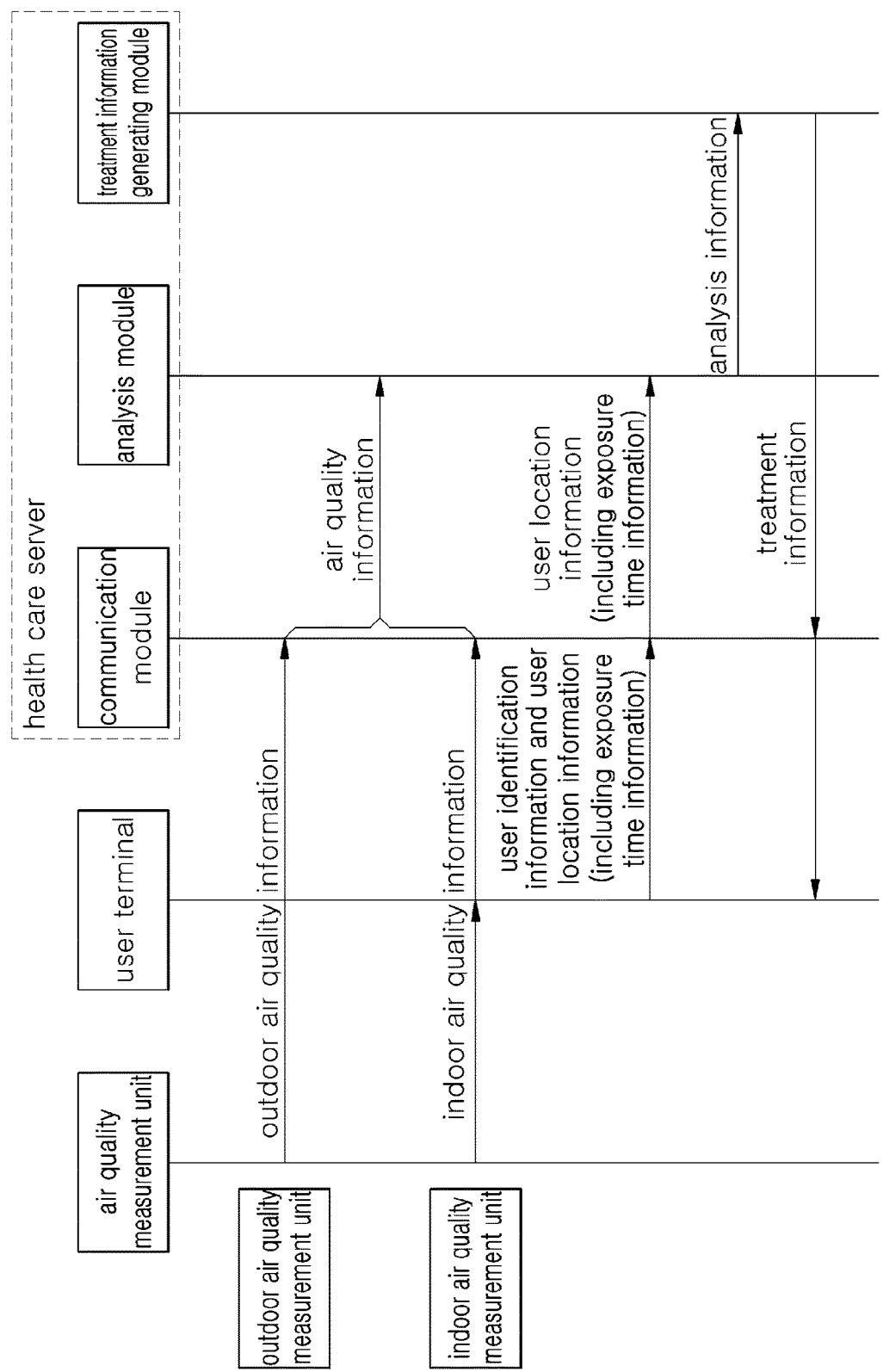
FIG. 6 is a view illustrating a first embodiment of a method of operating a health care system according to the present disclosure.
Figure 7:
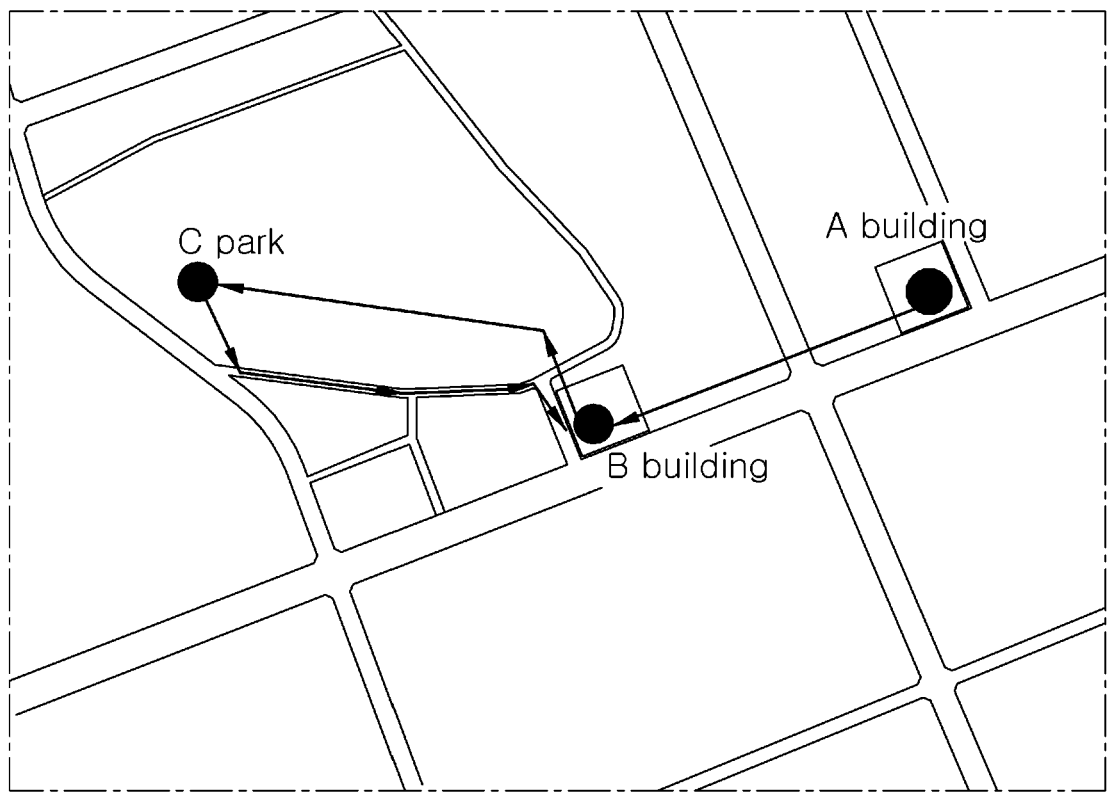
FIG. 7 is a view illustrating an example of a method of calculating an average air quality value from air quality information to derive analysis information by the health care server 100.

FIG. 6 is a view illustrating a first embodiment of a method of operating a health care system according to the present disclosure, and FIG. 7 is a view illustrating an example of a method in which the health care server 100 calculates an average air quality value from air quality information to derive analysis information.

As shown in FIG. 6, the health care server 100 may receive indoor air quality information or outdoor air quality information for a specific location from the indoor air quality measurement unit 400 of a space inside the building where the user is located or the outdoor air quality measurer 410 located in an area outside the building through the communication module 111.

In addition, the health care server 100 may receive user identification information, user location information, and exposure time information from the user terminal 200 through the communication module 111.

The health care server 100 may obtain air quality information of the specific location where the user is currently located based on the received user identification information and the user location information.

Here, the user location information may include not only a specific location in a specific place where the user is located but also a location movement path of a user who has moved from the specific location to another location, and may include a time taken for the user to move along the corresponding route or an exposure time route including a time during which the user has stayed at the specific location.

In particular, the health care server 100 may check air quality information for the specific location from the user location information and check how long the user has stayed at the specific location based on the exposure time information received together with the user location information to generate analysis information therefrom.

As an example, as shown in FIG. 7, if the user, who spent 1 hour inside building A (air quality information: good (◉)), spent 1 hour inside building B (air quality information: slightly poor (Δ)), spent 2 hours in park C (air quality information: normal (○)), and spent 1 hour in building B (air quality information: a slightly poor (Δ)), requests a treatment for the user's respiratory through the health care processing module 280 provided in the user terminal 200, the health care server 100 may determine time weight values (A: 0.2, B: 0.2, C: 0.4, and B: 0.2) at the specific locations by dividing each time (e.g., A: 1 hour, B: 1 hour, C: 2 hours, and B: 1 hour) during which the user is exposed to each specific location of the areas A, B, C, and B by a total time value (5 hours).

In addition, the health care server may determine an average air quality information value regarding the entire areas (A, B, and C) by including the time weight values (A: 0.2, B: 0.2, C: 0.4, and B: 0.2) at the specific locations in the air quality information value at each specific location. In this manner, analysis information may be derived using the derived average air quality information value and the total time value as factors of the analysis information.

For example, calculation may be performed such that inside of building A: good (◉)*0.2, inside of building B: slightly poor (Δ)*0.2, park C: normal (○)*0.4, inside of building B: slightly poor (Δ)*0.2. Accordingly, the health care server may calculate the analysis information by counting the average air quality information value as a factor of normal (○) and the exposure time information as a factor of 5 hours (a slightly long (Δ)).

However, the above method of deriving the analysis information is an example, and the present disclosure is not limited thereto. That is, the analysis information may be derived by including specific air quality information on specific air, for example, a concentration of fine dust or ultra-fine dust, a temperature, humidity, a concentration of oxygen, a concentration of carbon dioxide, a concentration of ozone, and the like as factors of the analysis information.

In this manner, the analysis information generated by the analysis module 113 of the health care server 100 may be input to the treatment information generating module 115, and the treatment information generating module 115 may generate treatment information including usage data regarding the complex treatment device 300 of the user using the derived analysis information.

Thereafter, the treatment information generated by the treatment information generating module 115 may be transmitted to the user terminal 200 through the communication module 111.

Here, the treatment information provided by the treatment information generating module 115 will be described in more detail below in FIG. 12.

Figure 8:
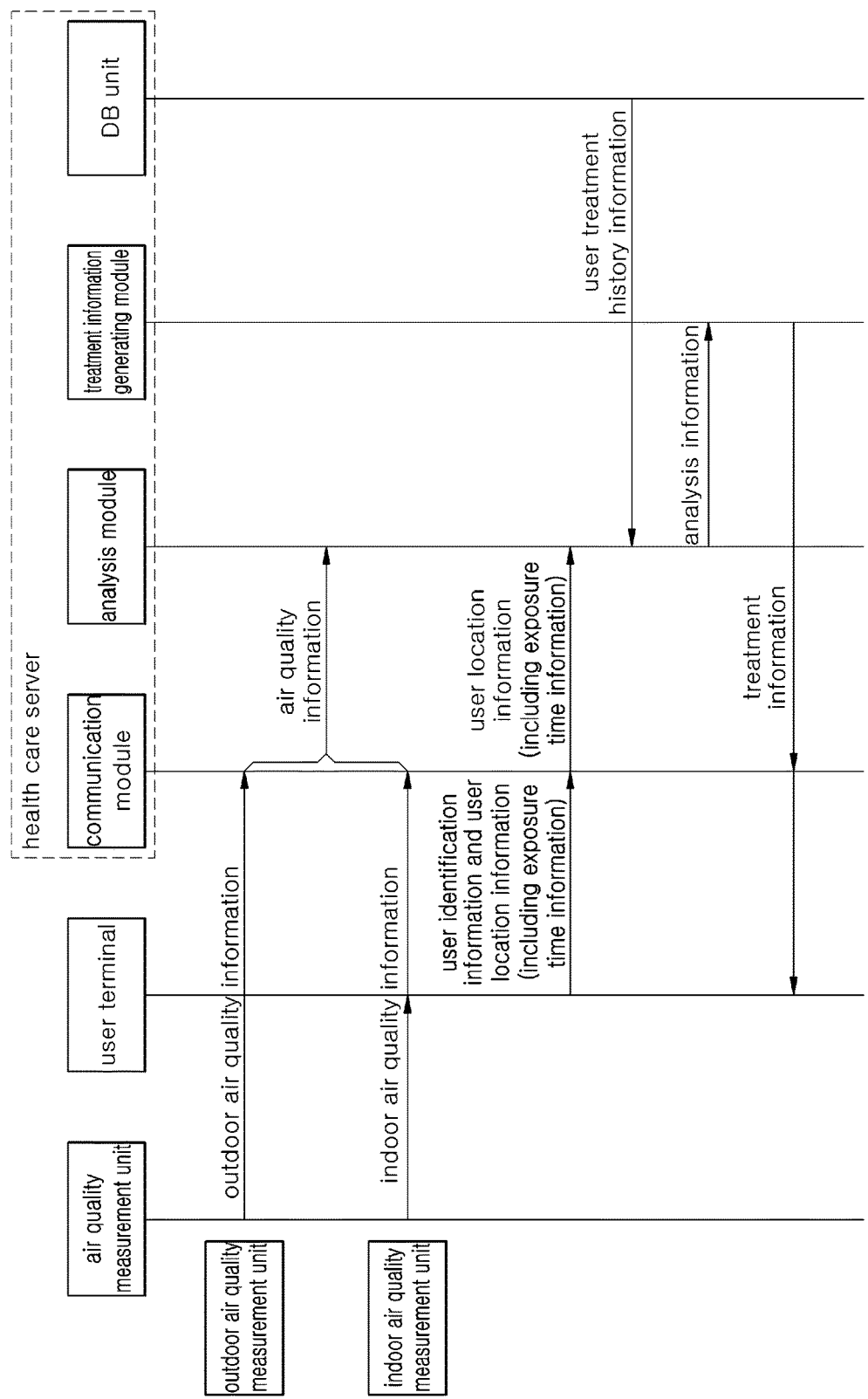
FIG. 8 is a view illustrating a second embodiment of a method of operating a health care system according to the present disclosure.

FIG. 8 is a view illustrating a second embodiment of a method of operating a health care system according to the present disclosure.

As shown in FIG. 8, when the user treatment history information stored in the DB unit 120, as well as the air quality information, the user identification information, and the exposure time information, is input to the analysis module 113, the analysis module 113 may derive analysis information by including the air quality information, the user location information, the exposure time information, and the user treatment history information as factors of the analysis information.

More specifically, the analysis module 113 may analyze the questionnaire information, the user image information, the respiratory volume information, and the past treatment history information previously stored in the health care server 100, along with the air quality information, the user location information, and the exposure time information, to analyze and derive the current user's respiratory status to generate the analysis information, and input the analysis information to the treatment information generating module 115. The treatment information generating module 115 may then transmit treatment information to the user terminal 200.

In this case, when the health care server 100 generates the analysis information, the health care server 100 may more precisely analyze the user's respiratory status and recognize a time at which the user had his respiratory system treated in the past and the user's respiratory status at that time, and thus, the health care server 100 may provide more precise treatment information to the user.

Figure 9:
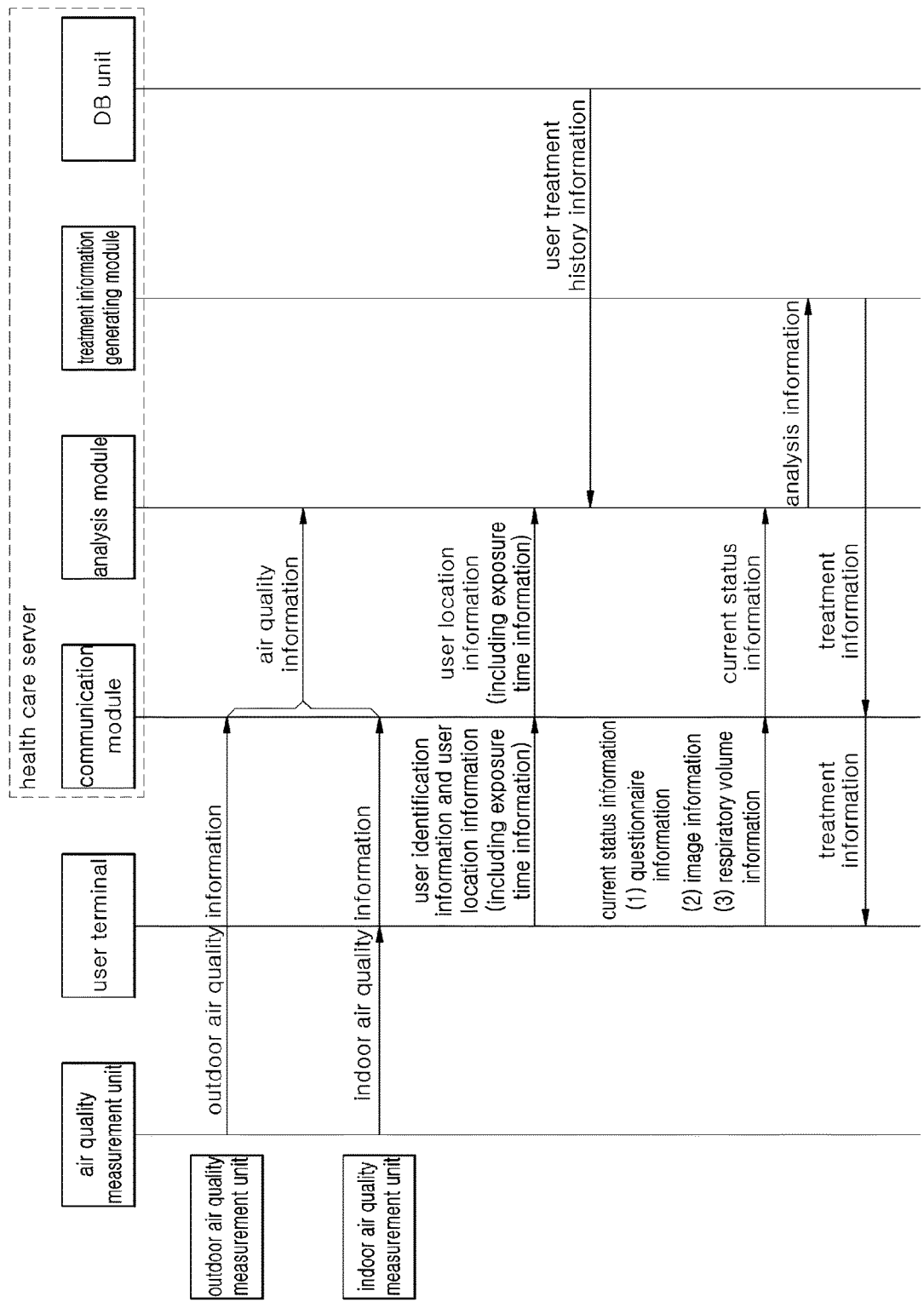
FIG. 9 is a view illustrating a third embodiment of a method of operating a health care system according to the present disclosure.

FIG. 9 is a view illustrating a third embodiment of a method of operating a health care system according to the present disclosure.

As shown in FIG. 9, when current status information is transmitted from the user terminal 200 to the analysis module 113 in addition to the air quality information, the user identification information, the exposure time information, and the user treatment history information, the analysis module 113 may derive analysis information by including the air quality information, the user location information, the exposure time information, the user treatment history information, and the current status information as factors of the analysis information.

Here, as described above, the current status information may include at least one of (1) questionnaire information on the current user's respiratory status, (2) user image information obtained by imaging at least one of the current user's oral cavity, nasal cavity, ear canal, eyes, or skin, or (3) the current user's respiratory volume, and the analysis module 113 may generate more accurate analysis information using the current status information as a factor of the analysis information in addition to the air quality information, the user identification information, the exposure time information, and the user treatment history information, and accordingly, the health care server 100 may provide more effective treatment information to the user.

In this case, when the health care server 100 generates the analysis information, the health care server 100 may more precisely analyze the user's current respiratory status and recognize a time at which the user had his respiratory system treated in the past and the user's respiratory status at that time, and thus, the health care server 100 may provide more precise treatment information to the user.

Figure 10:
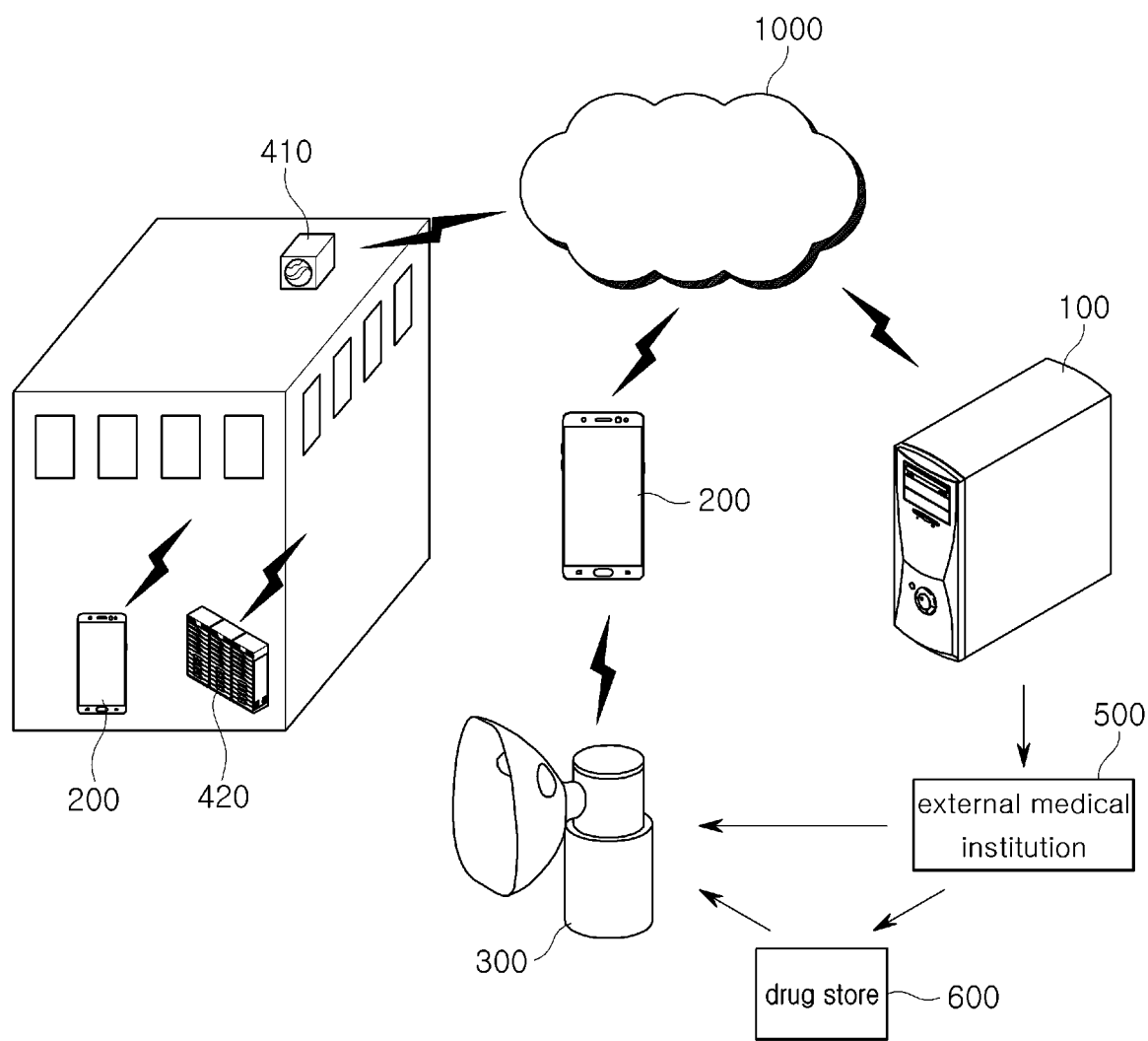
FIG. 10 is a view illustrating a health care system according to another example of the present disclosure.
Figure 11:
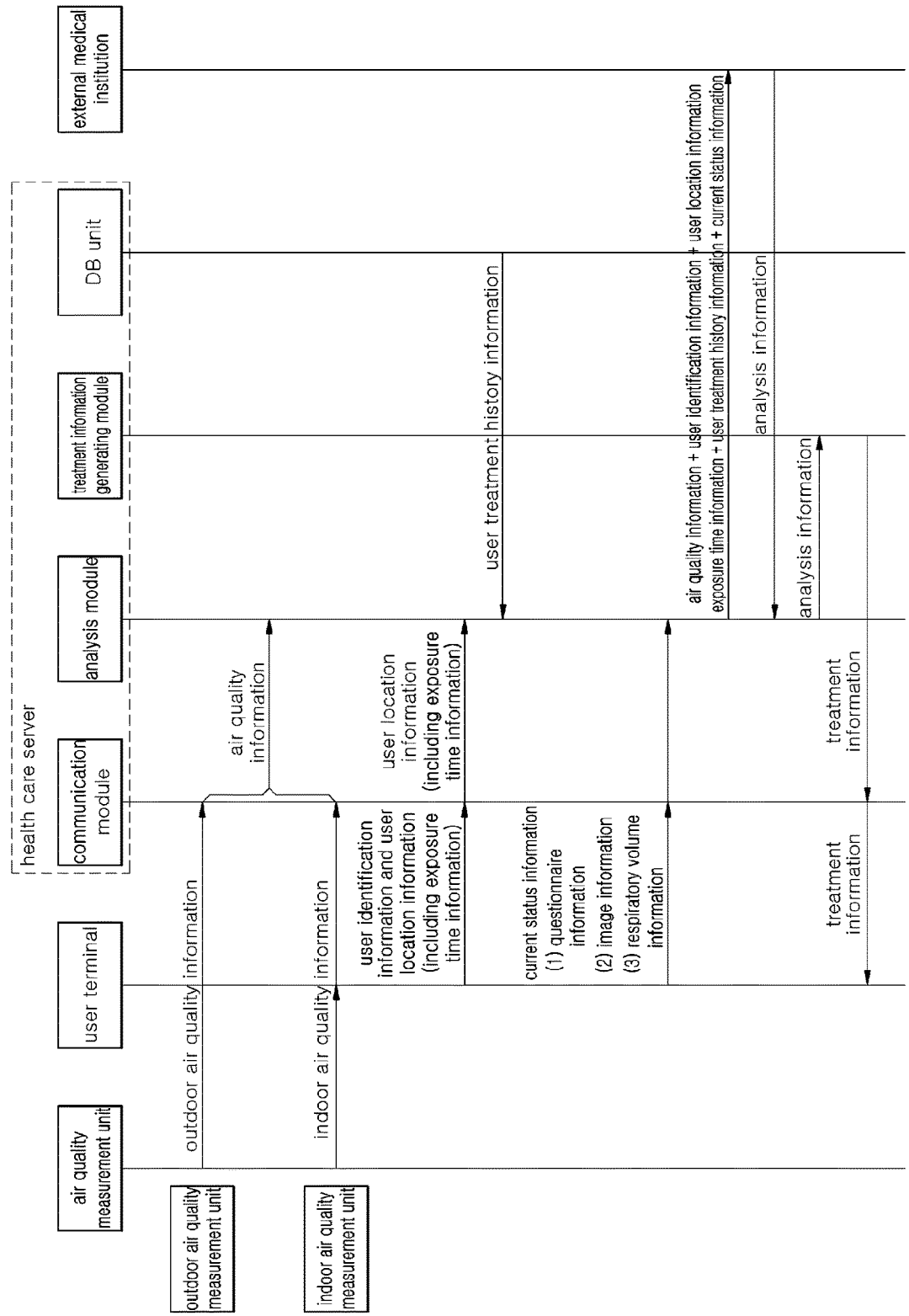
FIG. 11 is a view illustrating an example of a method of operating a health care system according to another example of the present disclosure.

FIG. 10 is a view illustrating a health care system according to another example of the present disclosure, and FIG. 11 is a view illustrating an example of a method of operating a health care system according to another example of the present disclosure.

In FIG. 10, descriptions of contents overlapping with those described in FIGS. 1 to 9 will be omitted or briefly described, and other parts will be mainly described.

As shown in FIG. 10, the health care system according to another example of the present disclosure includes an air quality measurement unit 400, a user terminal 200, a health care server 100, a complex treatment device 300, and an external medical institution 500.

The air quality measurement unit 400 may be located in at least one of the inside or outside of a building and may transmit air quality information on a corresponding area or a corresponding space to the health care server 100.

The user terminal 200 may transmit user identification information for identifying a user and user location information for a specific location in which the user is located to the health care server 100.

The health care server 100 may receive air quality information, the user identification information, and the user location information, provide at least one of the air quality information, user treatment history information, and current status information to an external source, receive analysis information analyzed from the external source using at least one information, and provide treatment information on the user's respiratory system.

The external medical institution 500 may receive at least one of the air quality information, the user treatment history information, and current status information from the health care server 100 and may transmit analysis information analyzed by diagnosing the user's respiratory status by a medical professional based on the information provided from the health care server 100 to the health care server 100 again.

To this end, as described above with reference to FIG. 3, the health care server 100 may include the remote diagnosis module 117 providing at least one of the air quality information, the user treatment history information, and the current status information to the outside and receive analysis information analyzed by diagnosing the user's respiratory status from the external medical institution 500.

As described above, when the remote diagnosis module 117 of the health care system according to another example of the present disclosure provides information for remote diagnosis to the external medical institution 500, the remote diagnosis module 117 may visualize the air quality information, the user treatment history information, and the current status information in the form of document, an image or a table and provide the same so that the external professional may easily determine the information.

As shown in FIG. 11, the remote diagnosis module 117 provided in the health care system according to another example of the present disclosure may receive the air quality information from the air quality measurement unit 400, the user identification information, the user location information including exposure time information, and the current status information from the user terminal 200, and receive the user treatment history information from the DB unit 120 of the health care server 100.

Thereafter, the remote diagnosis module 117 may process the air quality information, the user identification information, the user location information including the exposure time information, the user treatment history information, and the current status information to be documented and visualized, and provide the same to the external medical institution 500.

When the air quality information, the user identification information, the user location information including the exposure time information, user treatment history information, and the current status information are provided from the health care server 100, the medical professional in the external medical institution 500 may diagnose the user's respiratory status based on the provided information and transmit analysis information based on the diagnosis to the remote diagnosis module 117 of the health care server 100.

In this case, the analysis information provided by the external medical institution 500 may include drug prescription data and data regarding a prescription method for the user's respiratory system.

The remote diagnosis module 117 may input the analysis information provided from the external medical institution 500 to the treatment information generating module 115, and the treatment information generating module 115 may provide treatment information on the user's respiratory system to the user terminal 200 based on the analysis information provided from the external medical institution 500.

In addition, the remote diagnosis module 117 may update the analysis information provided from the external medical institution 500 to the DB unit 120 of the health care server 100.

In addition, in FIG. 11, a case where the health care server 100 receives the analysis information on the user from the external medical institution 500 and provides the treatment information to the user terminal 200 through remote diagnosis is described as an example, but the present disclosure is not limited thereto.

For example, while the health care server 100 provides the treatment information to the user terminal 200 and the external medical institution 500 based on the analysis information provided from the external medical institution 500, the user may visit the external medical institution on a specific date to get respiratory system treatment in the external medical institution 500, receive a drug prescription to be used for complex respiratory treatment from the external medical institution 500, receive the prescribed drug at the pharmacy 600, and use the complex treatment device 300 according to the treatment information.

In this way, the treatment information provided by the health care server 100 according to the present disclosure may be differentiated using at least one of the air quality information, the exposure time information, the user treatment history information, and the current status information included in the analysis information so as to be provided.

More specifically, in the treatment information, information on a usage time or a usage number for at least one of the nebulizer E1, the injector E2, the inhaler E3, and the rhinitis treatment instrument E4 included in the complex treatment device 300 may be provided to be different according to at least one information.

Hereinafter, various examples in which the information on the usage time or the usage number for at least one of the nebulizer E1, the injector E2, the inhaler E3, and the rhinitis treatment instrument E4 is provided to be different according to at least one of the air quality information, the exposure time information, the user treatment history information, or the current status information will be described.

FIG. 12 is a view illustrating a first embodiment of treatment information provided by the health care server 100 according to the present disclosure, FIG. 13 is a view illustrating a second embodiment of treatment information provided by the health care server 100 according to the present disclosure, and FIG. 14 is a view illustrating a third embodiment of treatment information provided by the health care server 100 according to the present disclosure.

As shown in FIG. 12, the first embodiment of the treatment information provided by the health care server 100 may provide treatment information using analysis information analyzed with the air quality information, the user location information, and the exposure time information.

For example, the air quality information may be classified into good (⊚), normal (○), slightly poor (Δ), and very poor (X), and the exposure time information may be classified into short (⊚), normal (○), and slightly longer (Δ), and very long (X).

In addition, a case where the treatment instrument 320 of the complex treatment device 300 includes all of the nebulizer E1, the injector E2, the inhaler E3, and the rhinitis treatment instrument E4 is illustrated as an example.

According to the air quality information and the exposure time information classified in this manner, the information on the usage time or usage number of the complex treatment device 300 of the user may be differentiated and provided to the user terminal 200 or the complex treatment device 300.

In addition, the user's respiratory status may be analyzed in consideration of the air quality information and the exposure time information, and different treatment programs may be provided according to the corresponding respiratory status.

For example, as described in FIG. 7, when analysis information in which the user location information and the exposure time information are A (1 hour)/B(1 hour)/C (2 hours)/B (1 hour), and the indoor air quality information of A is good. (⊚), the indoor air quality information of B is slightly poor (Δ), the outdoor air quality information of C is normal (○), an average air quality value of specific locations A, B, and C is normal (○), and the exposure time information is 5 hours (slightly long A) is provided, the health care server 100 may provide treatment information in which the nebulizer E1 is carried out 2 minutes 2 times (twice) and the injector E2 1 is carried out 1 minute and 1 time (once) according to the corresponding analysis information.

If the average air quality value of the air quality information is calculated as slightly poor (Δ), the treatment information may be provided to be differentiated such that nebulizer E1 2 minutes 2 times, injector E2 2 minutes 2 times, inhaler E3 1 minute 1 time, rhinitis treatment instrument E4 1 minute and 1 time.

In addition, as shown in FIG. 13, in a second embodiment of the treatment information provided by the health care server 100 according to the present disclosure, treatment information may be provided using analysis information further including user treatment information history in addition to the air quality information, the user identification information, and the exposure time information.

Here, the user treatment history information may be classified into, for example, a diagnosis history and a treatment history. The diagnosis history may be classified into better (⊚), maintained (○), worse (Δ), and very deteriorated (X), and the treatment history may be classified into 1 day ago, 2 days ago, 3 days ago, and 4 days ago.

The factors used for the health care server 100 to generate the analysis information may further include user treatment history information including the diagnosis history and the treatment history.

User treatment history information including diagnosis history and treatment history may be further added to the factor used to generate the analysis information by the health care server 100.

In FIG. 13, since both the diagnosis history and the treatment history cannot be displayed, a case where the diagnosis history is maintained (○) and the treatment history is 3 days ago is illustrated as an example.

If at least one of the diagnosis history and the treatment history has a different value, the treatment information disclosed as an example in FIG. 13 may be completely different.

In addition, if the treatment history is, for example, one day ago, the health care server 100 may provide information on a usage time or a usage number of the complex treatment device 300 as treatment information and may provide information recommending that the complex treatment device 300 should be used in 1 day or 2 days together.

A third embodiment of the treatment information provided by the health care server 100 according to the present disclosure may provide treatment information using analysis information further including current status information, as well as the air quality information, the user location information, the exposure time information, and the user treatment information history, as shown in FIG. 14.

As described above, the current status information of the user may be a result value including at least one of (1) questionnaire information on the current user's respiratory status, (2) user image information obtained by imaging the current user's oral cavity, nasal cavity, eyes, ear canal, or skin, or (3) the current user's respiratory volume.

Comprehensive result values for the current status information may be calculated and classified into any one of good (⊚), normal (○), slightly serious (Δ), and very serious (X).

Accordingly, the health care server 100 according to the present disclosure may generate analysis information using even the current status information of the user's respiratory system as a factor, generate treatment information based thereon, and provide information differentiated in the usage time or usage number of the complex treatment device 300 to the user terminal 200 or the complex treatment device 300, thereby guiding more precise and effective treatment to be performed on the user's respiratory system.

FIGS. 15 to 18 show examples of contents of treatment information provided by the health care server 100 according to the present disclosure, but hereinafter, examples of types of treatment information provided by the health care server 100 will be described.

Figure 16:
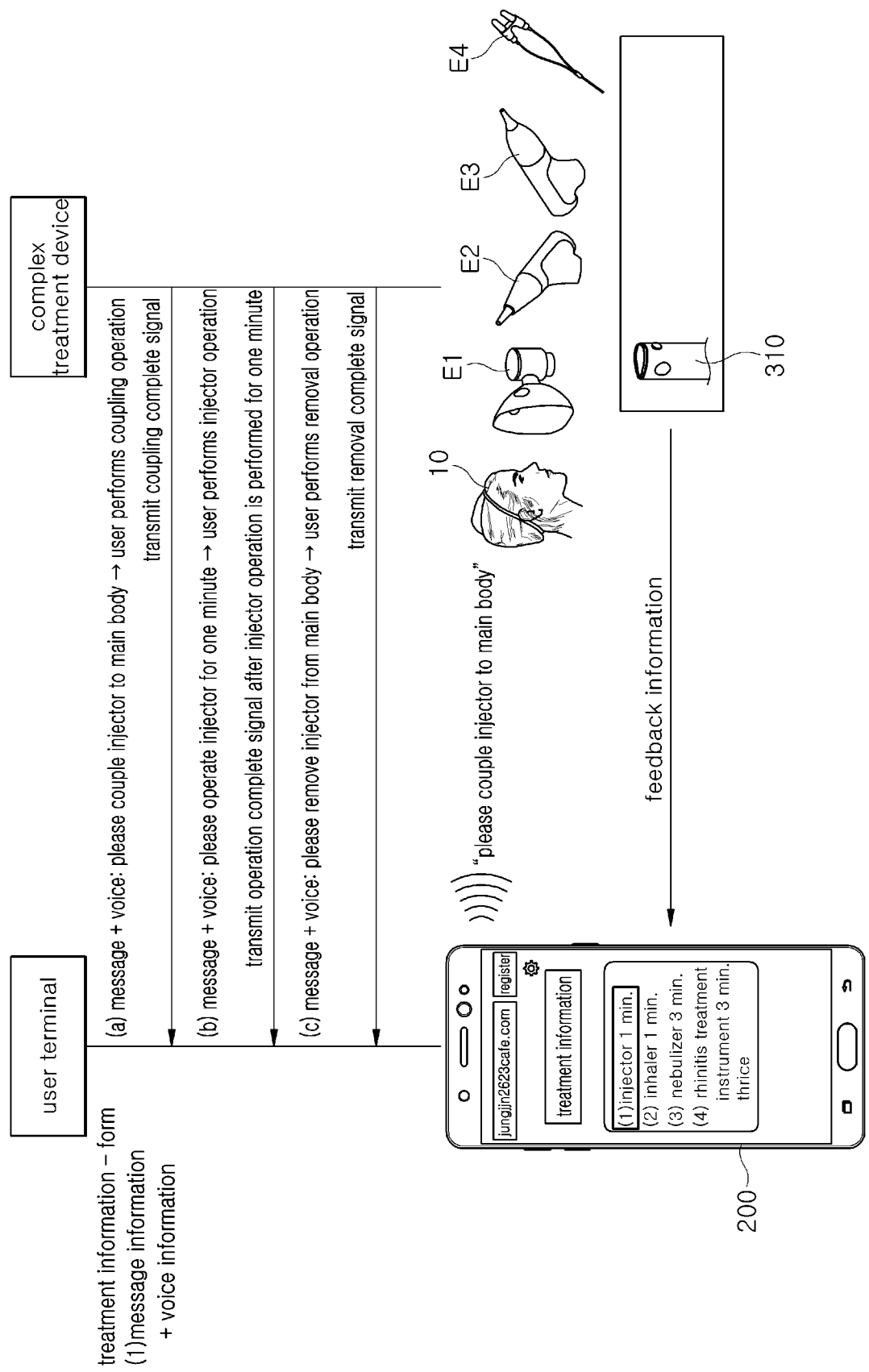
FIG. 16 is a view illustrating an example of an operation between the user terminal 200 and the complex treatment device 300 when the health care server 100 according to an example of the present disclosure provides treatment information in the form of message information and voice information to the user terminal 200.
Figure 17:
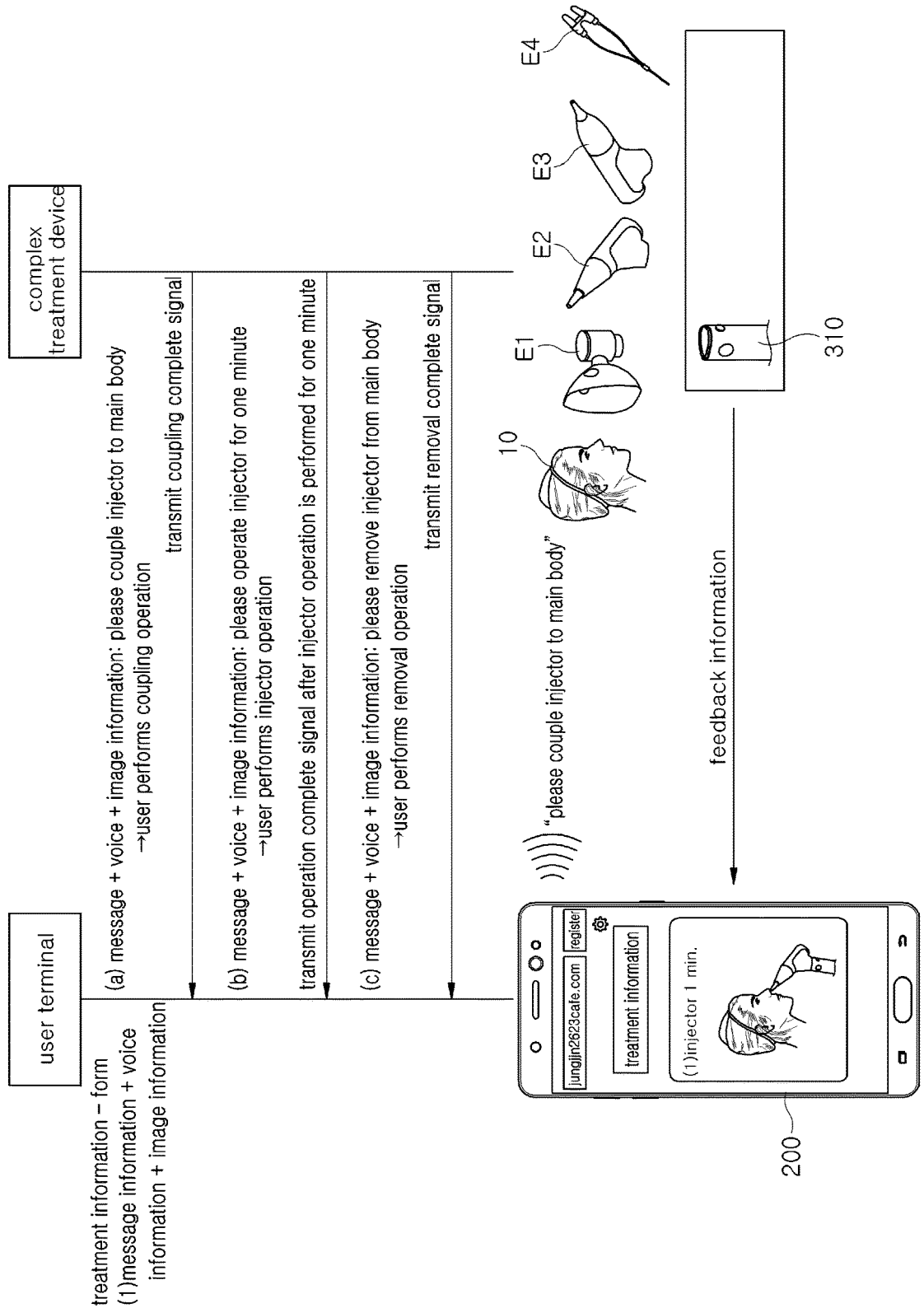
FIG. 17 is a view illustrating an example of an operation between the user terminal 200 and the complex treatment device 300 when the health care server 100 according to an example of the present disclosure provides treatment information in the form of message information, voice information, and image information to the user terminal 200.
Figure 18:
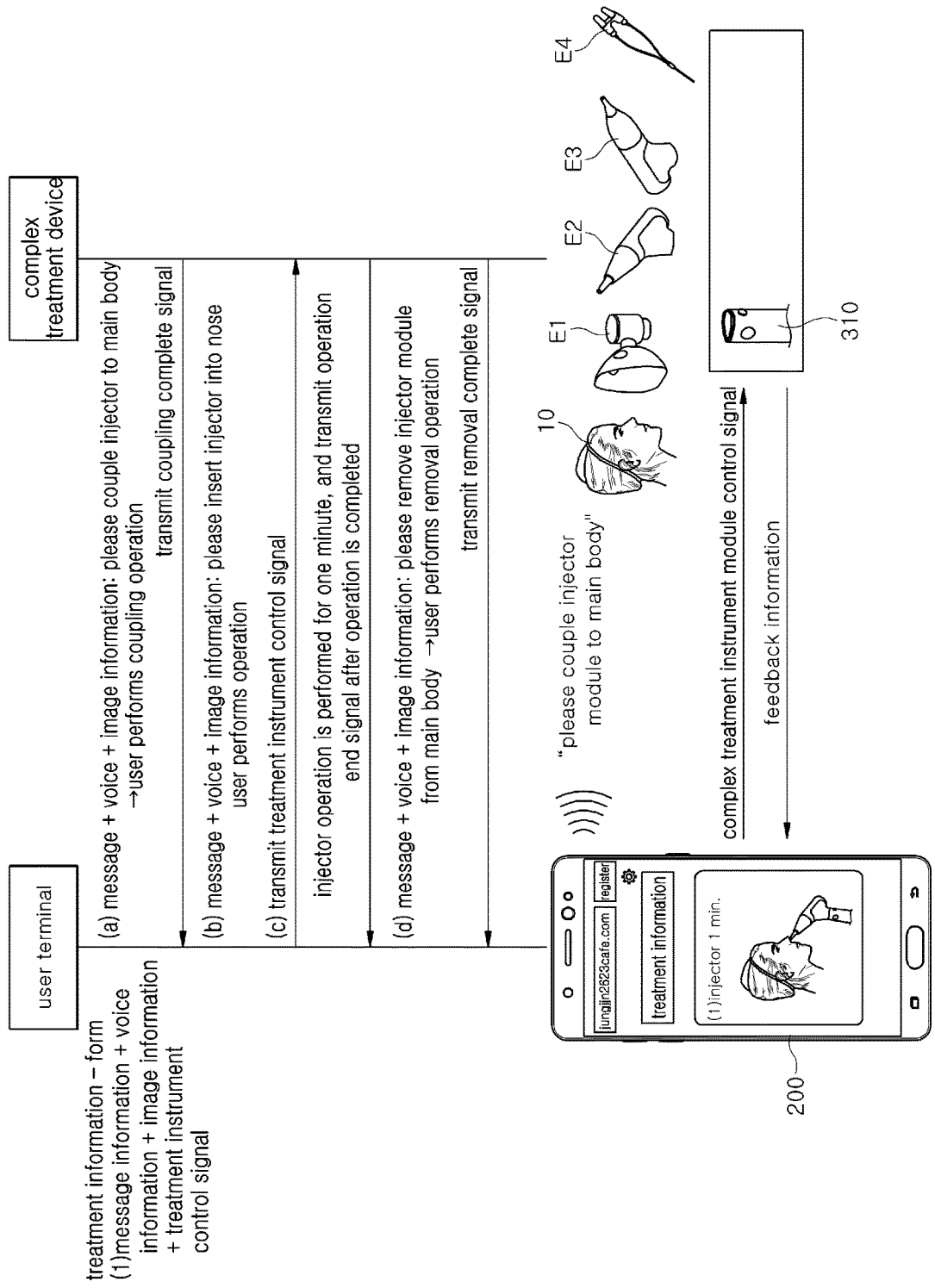
FIG. 18 is a view illustrating an example of an operation between the user terminal 200 and the complex treatment device 300 when the health care server 100 according to an example of the present disclosure provides treatment information in the form of message information, voice information, image information, and a treatment instrument control signal to the user terminal 200.

FIG. 15 is a view illustrating types of treatment information provided by the health care server 100 according to an example of the present disclosure, FIG. 16 is a view illustrating operation examples of the user terminal 200 and the complex treatment device 300 when the health care server 100 according to an example of the present disclosure provides treatment information in the form of message information and voice information to the user terminal 200, FIG. 17 is a view illustrating operation examples of the user terminal 200 and the complex treatment device 300 when the health care server 100 according to an example of the present disclosure provides treatment information in the form of message information, voice information, and image information, and FIG. 18 is a view illustrating operation examples of the user terminal 200 and the complex treatment device 300 when the health care server 100 according to an example of the present disclosure provides treatment information in the form of message information, voice information, image information, and a treatment instrument control signal.

As shown in FIG. 15, the health care server 100 may provide treatment information to the user terminal 200 in three forms.

For example, treatment information may be provided in at least one of forms of (1) message information or voice information output through a health care application program of the user terminal 200, (2) image or video information displayed through the health care application program of the user terminal 200, and (3) a treatment instrument control signal for controlling the complex treatment device 300 through the health care application program of the user terminal 200.

When the user terminal 200 receives the treatment information and the user performs an operation of the complex treatment device 300 according to the received treatment information, the complex treatment device 300 may transmit feedback information on an operation result of the complex treatment device 300 to the user terminal 200.

That is, when the user uses at least one of the nebulizer E1, the injector E2, the inhaler E3, and the rhinitis treatment instrument E4 provided in the complex treatment device 300, the complex treatment device 300 may provide feedback information on at least one of the nebulizer. E1, the used injector E2, the inhaler E3, and the rhinitis treatment instrument E4 to the user terminal 200. The user terminal 200 may transmit the feedback information to the health care server 100, and the health care server 100 may store the received feedback information in the user treatment history information DB 121c of the DB unit 120.

The feedback information may include at least one of a coupling complete signal when the treatment instrument 320 is inserted into the main body 310, an operation time and operation end signal for operating the treatment instrument 320, and a removal complete signal when the treatment instrument 320 is separated from the main body 310.

More specifically, as shown in FIG. 16, when treatment information in the form of message information and voice information is provided from the health care server 100 to the user terminal 200, the treatment information may be displayed in the form of a message for an operation of each treatment instrument 320 on the user terminal 200, and while message information on any one treatment instrument 320 is highlighted and displayed, detailed information on the message information of the corresponding treatment instrument 320 may be output in the form of voice information.

Here, the voice information may basically include language information that may be recognized by a person, but the present disclosure is not limited thereto, and the voice information may include melody or other sound information that does not include a language, if necessary.

For example, in a state where information of (1) injector E2 1 minute, (2) inhaler E3 1 minute, (3) nebulizer E1 3 minutes, (4) rhinitis treatment instrument E4 3 minutes is given as treatment information, while message information of (1) injector E2 1 minute is highlighted and displayed, voice information (a) "please couple the injector E2 module to the main body 310" may be output through the user terminal 200. Here, when the user performs an operation of coupling the injector E2 to the main body 310 of the complex treatment device 300, the complex treatment device 300 may transmit a coupling complete signal according to coupling of the injector E2 as feedback information.

Thereafter, in a state where (1) the message information of injector E2 1 minute is highlighted and displayed, the user terminal 200 may output (b) voice information such as "please operate injector E2 for 1 minute". The user may operate the injector E2 of the complex treatment device 300 for 1 minute and subsequently terminates the operation, the complex treatment device 300 may transmit a signal for the injector E2 operation time and operation completion as feedback information.

Thereafter, in a state where (1) the message information of (1) injector E2 1 minute is highlighted and displayed, the user terminal 200 may output voice information of (c)

"please remove injector E2 from main body 310". When the user performs an operation of removing the injector E2 of the complex treatment device 300 from the main body 310, the complex treatment device 300 may transmit a signal for completion of injector E2 removal as feedback information.

Thereafter, message information for (2) inhaler E3 1 minute, (3) nebulizer E1 3 minutes, and (4) rhinitis treatment instrument E4 3 minutes displayed on the user terminal 200 may also be processed in the same manner as described above.

In addition, as shown in FIG. 17, when the health care server 100 provides treatment information in the form of message information, voice information, and image information to the user terminal 200, the user terminal 200 may display message information and image information for a corresponding treatment instrument 320 to perform, for example, (1) injector E2 1 minute operation and simultaneously output detailed information on the message information of the corresponding treatment instrument 320 in the form of voice information such as (a), (b), and (c).

Alternatively, the user terminal 200 may display message information on the corresponding treatment instrument 320 to perform the operation and simultaneously output detailed information on the message information of the treatment instrument 320 in the form of image information and voice information.

In addition, as shown in FIG. 18, when the health care server 100 provides treatment information to the user terminal 200 in the form of message information, voice information, image information, and a treatment instrument control signal, the user terminal 200 may display message information and image information on the corresponding treatment instrument 320 to perform the operation and simultaneously display detailed information on the message information of the corresponding treatment instrument 320 in the form of voice information as shown in (a) and (b) of FIG. 18.

More specifically, (a) after the injector E2 of the complex treatment device 300 is coupled to the main body 310, (b) when the user performs an operation of inserting the complex treatment device 300 into the nose, a signal for operating the injector E2 for 1 minute may be transmitted as a treatment instrument control signal through the user terminal 200.

Accordingly, the complex treatment device 300 may perform an operation of the injector E2 for 1 minute according to the treatment instrument control signal, terminates the operation of the injector E2 according to the treatment instrument control signal after performing the operation for 1 minute, and transmit feedback information to the user terminal 200.

The user terminal 200 may transmit the feedback information of the complex treatment device 300 to the health care server 100, and the health care server 100 may update the feedback information of the complex treatment device 300 to the user treatment history information.

Here, as described above with reference to FIGS. 16 to 18, an interface between the user terminal 200 and the complex treatment device 300 providing treatment information and feedback information may be implemented in the form of a game for children.

As an example, as the health care application program is executed on the user terminal 200, an image of a cartoon character performing the complex treatment device 300 is displayed on the user terminal 200. When a child or a toddler as a user operates the complex treatment device 300, the user terminal 200 may receive feedback information from the complex treatment device 300 and display an image for providing a point on a game to the cartoon character or rewarding.

According to the health care system, the health care server 100, and the control method of the health care server 100 according to an example of the present disclosure, since the health care server 100 provides treatment information on the user's respiratory system analyzed and processed from air quality information on a specific location, which is an area or space where the user is located, the user may more conveniently treat and manage his or her respiratory system.

The present disclosure is not limited to the embodiments described above and the accompanying drawings, and various modifications and variations may be made from the viewpoint of a person skilled in the art to which the present invention pertains. Therefore, the scope of the present disclosure should be defined by the equivalents of claims of the present disclosure as well as the claims.

The invention claimed is:

1. A health care system for providing respiratory treatment information using air quality information, the health care system comprising:
    an air quality measurement unit located in at least one of the inside or outside of a building and configured to transmit air quality information on a specific location, which is an area or space in which a user is located;
    a user terminal configured to transmit user identification information for identifying the user and user location information on a specific location where the user is located; and
    a health care server configured to receive the air quality information, the user identification information, and the user location information, to identify the user's movement path based on the user location information, to calculate individual time weights for each of the user's movement path by dividing each time during which the user is exposed to each of the specific location by a total exposure time, to incorporate each of the individual time weights into the air quality information for each movement path to calculate an average air quality information value for each movement, to generate analysis information using the average air quality information value and the total exposure time, and to provide treatment information to operate a complex treatment device comprising a main body capable of communicating with the user terminal and a treatment instrument capable of communicating with the main body or the user terminal and performing a respiratory treatment on at least one of the user's ear canal, oral cavity, eyes, or nasal cavity and the treatment instrument comprising a nebulizer, an injector, a low-power light irradiator, and an inhaler, based on the analysis information,
    wherein the treatment information includes information on usage time and usage number for each of the nebulizer, the injector, the low-power light irradiator, and the inhaler, and each of the usage time and usage number is determined depending on type of the treatment instrument, the average air quality information value and the total exposure time.

2. The health care system of claim 1, wherein
    the air quality information is transmitted from the air quality measurement unit to the health care server through a communication network linked with the air quality measurement unit or is transmitted from the air quality measurement unit to the health care server through the user terminal.

3. The health care system of claim 1, wherein
the user location information transmitted by the user terminal further includes exposure time information on a time during which the user is exposed to the specific location.

4. The health care system of claim 3, wherein
the health care server comprises:
a health care controller configured to provide the treatment information using the analysis information analyzed from the air quality information, the user location information, and the exposure time information; and
a database (DB) unit configured to store the air quality information, the user identification information, the user location information, and the exposure time information,
wherein the health care controller comprises:
a communication module configured to receive the air quality information, the user identification information, the user location information, and the exposure time information;
an analysis module configured to analyze the air quality information, the user location information, and the exposure time information to generate analysis information on the user's respiratory status; and
a treatment information generating module configured to generate treatment information on the user's respiratory system using the analysis information, and
wherein
the DB unit comprises:
a user identification information DB configured to store the user identification information; a user location information DB configured to store the user location information and the exposure time information;
a user treatment history information DB configured to store user treatment history information on the user's respiratory system; and
an air quality information DB configured to store the air quality information.

5. The health care system of claim 4, wherein
the user identification information includes at least an ID of the user for identifying the user, and when the user terminal is first registered in the health care server, the user terminal transmits at least one of the user ID, the user's name, the user's age, and the user's gender to the health care server.

6. The health care system of claim 4, wherein,
when the user terminal is first registered in the health care server, the user terminal further transmits questionnaire information on the user's respiratory status and past treatment history of the user's respiratory system performed prior to registration to the health care server to the health care server and the health care server updates the user treatment history information with the questionnaire information and the past treatment history information.

7. The health care system of claim 4, wherein
the health care server generates the analysis information using the air quality information, the user location information, the exposure time information, and the user treatment history information.

8. The health care system of claim 4, wherein
the user terminal transmits current status information on the user's respiratory status to the health care server.

9. The health care system of claim 8, wherein
the current status information includes (1) questionnaire information on the current user's respiratory status, (2) user image information obtained by imaging at least one of the current user's oral cavity, nasal cavity, eyes, ear canal, or skin, or (3) the current user's respiratory volume.

10. The health care system of claim 8, wherein
the health care server updates the user treatment history information with the current status information provided from the user terminal and generates the analysis information using the air quality information, the user location information, the exposure time information, the user treatment history information, and the current status information.

11. The health care system of claim 4, further comprising:
the complex treatment device capable of performing a respiratory treatment on at least one of the user's ear canal, oral cavity, eyes, or nasal cavity by interworking with the user terminal or the health care server,
wherein the user terminal has a health care application program linked with the complex treatment device.

12. The health care system of claim 1, wherein the health care server provides the treatment information differentiated using at least one of the air quality information, the exposure time information, the user treatment history information, or the current status information included in the analysis information, and
in the treatment information, information on a usage time or the number of times of use of at least one of the nebulizer, the injector, the low-power light irradiator, and the inhaler included in the complex treatment device is provided to be different according to the at least one information.

13. The health care system of claim 1, wherein
the treatment information is provided in at least one of forms of (1) message information or voice information output through the health care application program of the user terminal, (2) image or video information displayed through the health care application program of the user terminal, and (3) a treatment instrument control signal for controlling the complex treatment device through the health care application program of the user terminal.

14. The health care system of claim 1, wherein,
when the user performs an operation of the complex treatment device according to the treatment information, the complex treatment device transmits feedback information on an operation result of the complex treatment device to the user terminal.

15. The health care system of claim 14, wherein
the feedback information includes at least one of a coupling completion signal when the treatment instrument is inserted into the main body, an operation time and operation end signal for operating the treatment instrument, and a removal completion signal when the treatment instrument is separated from the main body.

16. A health care server for providing respiratory treatment information using air quality information, the health care server comprising:
a database (DB) unit configured to receive and store air quality information on at least one specific location inside or outside a building where a user is located, user identification information for identifying the user, and user location information; and
a health care controller configured to receive the air quality information, the user identification information, and the user location information and to identify the user's movement path based on the user location information, to calculate individual time weights for each of the user's movement path by dividing each time during which the user is exposed to each of the specific location by a total exposure time, to incorporate each of the individual time weights into the air quality information for each movement path to calculate an average air quality information value for each movement, to generate analysis information using the average air quality information value and the total exposure time, and to provide treatment information to operate a complex treatment device comprising a main body capable of communicating with the user terminal and a treatment instrument capable of communicating with the main body or the user terminal and performing a respiratory treatment on at least one of the user's ear canal, oral cavity, eyes, or nasal cavity and the treatment instrument comprising a nebulizer, an injector, a low-power light irradiator, and an inhaler, based on the analysis information, wherein the treatment information includes information on usage time and usage number for each of the nebulizer, the injector, the low-power light irradiator, and the inhaler, and each of the usage time and usage number is determined depending on type of the treatment instrument, the average air quality information value and the total exposure time.

17. The health care server of claim 16, wherein
the health care controller generates the analysis information using the air quality information, the user location information, and the exposure time information.

18. The health care server of claim 16, wherein
the health care controller comprises:
a communication module configured to receive the air quality information, the user identification information, the user location information, and the exposure time information;
an analysis module configured to analyze the air quality information, the user location information, and the exposure time information to generate analysis information on the user's respiratory status; and
a treatment information generating module configured to generate treatment information on the user's respiratory system using the analysis information, and
the DB unit comprises:
a user identification information DB configured to store the user identification information;
a user location information DB configured to store the user location information and the exposure time information;
a user treatment history information DB configured to store user treatment history information on the user's respiratory system; and
an air quality information DB configured to store the air quality information.

19. The health care server of claim 18, wherein
the health care controller further receives initial questionnaire information on the user's respiratory status and past treatment history for the user's respiratory system performed prior to registration to the health care server and updates the questionnaire information and the past treatment history information to the DB unit.

20. The health care server of claim 18, wherein
the health care controller generates the analysis information using the air quality information, the user location information, the exposure time information, and the user treatment history information.

21. The health care server of claim 18, wherein
the health care controller receives current status information on the user's respiratory status.

22. The health care server of claim 21, wherein
the current status information includes (1) questionnaire information on the current user's respiratory status, (2) user image information obtained by imaging at least one of the current user's oral, nasal, eye, ear canal, or skin, or (3) the current user's respiratory volume.

23. The health care server of claim 21, wherein
the health care controller provides the treatment information differentiated using at least one of the air quality information, the exposure time information, the user treatment history information, or the current status information included in the analysis information, and in the treatment information, information on a usage time or the number of times of use of at least one of treatment instruments among a nebulizer, an injector, a low-power light irradiator, and an inhaler is different for each treatment instrument.

24. The health care server of claim 23, wherein
the treatment information is provided in at least one of (1) a form of message information or voice information, (2) a form of image or video information, and (3) a form of a treatment instrument control signal for controlling the complex treatment device.

25. The health care server of claim 24, wherein
the health care controller receives feedback information on an operation result of the complex treatment device after the complex treatment device completes the operation according to the treatment information.

26. The health care server of claim 25, wherein
the feedback information includes at least one of a coupling completion signal when the treatment instrument is inserted into the main body, an operation time and operation end signal for operating the treatment instrument, and a removal completion signal when the treatment instrument is separated from the main body.

27. A health care method for providing respiratory treatment information using air quality information, the health care method comprising:
receiving, by a health care server, air quality information on at least one specific location inside or outside a building where a user is located, user identification information for identifying the user, and user location information; and
receiving, by the health care server, the air quality information, the user identification information, and the user location information, identifying the user's movement path based on the user location information, calculating individual time weights for each of the user's movement path by dividing each time during which the user is exposed to each of the specific location by a total exposure time, incorporating each of the individual time weights into the air quality information for each movement path to calculate an average air quality information value for each movement, generating analysis information using the average air quality information value and the total exposure time, and providing treatment information to operate a complex treatment device comprising a main body capable of communicating with the user terminal and a treatment instrument capable of communicating with the main body or the user terminal and performing a respiratory treatment on at least one of the user's ear canal, oral cavity, eyes, or nasal cavity and the treatment instrument comprising a nebulizer, an injector, a low-power light irradiator, and an inhaler, based on the analysis information, wherein the treatment information includes information on usage time and usage number for each of the nebulizer, the injector, the low-power light irradiator, and the inhaler, and each of the usage time and usage number is determined depending on type of the treatment instrument, the average air quality information value and the total exposure time.

28. The health care method of claim 27, wherein the analysis information is generated using the air quality information, the user location information, and the exposure time information.

29. The health care method of claim 27, wherein the health care server further receives initial questionnaire information on the user's respiratory status and past treatment history regarding the user's respiratory system performed prior to registration to the health care server and stores and updates the questionnaire information and the past treatment history information as user treatment history information.

30. The health care method of claim 29, wherein the health care server generates the analysis information using the air quality information, the user location information, the exposure time information, and the user treatment history information.

31. The health care method of claim 29, wherein the health care server further receives current status information on the user's respiratory status.

32. The health care method of claim 31, wherein the current status information includes (1) questionnaire information on the current user's respiratory status, (2) user image information obtained by imaging at least one of the current user's oral cavity, nasal cavity, ear canal, eyes, or skin, or (3) the current user's respiratory volume.

33. The health care method of claim 31, wherein the health care server stores the current status information and generates analysis information using the air quality information, the user location information, the exposure time information, the user treatment history information, and the current status information.

34. The health care method of claim 31, wherein the health care server provides the treatment information differentiated using at least one of the air quality information, the exposure time information, the user treatment history information, or the current status information included in the analysis information, and in the treatment information, information on a usage time or the number of times of use of at least one of treatment instruments among a nebulizer, an injector, a low-power light irradiator, and an inhaler is different for each treatment instrument.

35. The health care method of claim 34, wherein the treatment information is provided in at least one of (1) a form of message information or voice information, (2) a form of image or video information, and (3) a form of a treatment instrument control signal for controlling the complex treatment device.

36. The health care method of claim 35, wherein the health care server receives feedback information on an operation result of the complex treatment device after the complex treatment device completes the operation according to the treatment information.

37. The health care method of claim 36, wherein the feedback information includes at least one of a coupling completion signal when the treatment instrument is inserted into the main body, an operation time and operation end signal for operating the treatment instrument, and a removal completion signal when the treatment instrument is separated from the main body.

* * * * *